United States Patent
Dickinson et al.

(10) Patent No.: US 11,913,081 B2
(45) Date of Patent: Feb. 27, 2024

(54) PROXIMITY-DEPENDENT SPLIT RNA POLYMERASES AS A VERSATILE BIOSENSOR PLATFORM

(71) Applicant: The University of Chicago, Chicago, IL (US)

(72) Inventors: Bryan C. Dickinson, Chicago, IL (US); Jinyue Pu, Chicago, IL (US); Julia Zinkus, Chicago, IL (US)

(73) Assignee: The University of Chicago, Chicago, IL (US)

(*) Notice: Subject to any disclaimer, the term of this patent is extended or adjusted under 35 U.S.C. 154(b) by 1129 days.

(21) Appl. No.: 16/305,298

(22) PCT Filed: Jun. 6, 2017

(86) PCT No.: PCT/IB2017/053324
§ 371 (c)(1),
(2) Date: Nov. 28, 2018

(87) PCT Pub. No.: WO2017/212400
PCT Pub. Date: Dec. 14, 2017

(65) Prior Publication Data
US 2020/0332371 A1    Oct. 22, 2020

Related U.S. Application Data

(60) Provisional application No. 62/424,875, filed on Nov. 21, 2016, provisional application No. 62/346,174, filed on Jun. 6, 2016.

(51) Int. Cl.
*C12Q 1/6897* (2018.01)
*C12N 9/12* (2006.01)
*C12Q 1/689* (2018.01)
*C12Q 1/48* (2006.01)

(52) U.S. Cl.
CPC ......... *C12Q 1/6897* (2013.01); *C12N 9/1247* (2013.01); *C12Q 1/48* (2013.01); *C12Q 1/689* (2013.01); *C12Y 207/07006* (2013.01)

(58) Field of Classification Search
None
See application file for complete search history.

(56) References Cited

U.S. PATENT DOCUMENTS

| | | |
|---|---|---|
| 9,394,537 B2 | 7/2016 | Liu et al. |
| 2009/0061426 A1 | 3/2009 | Belyaev et al. |
| 2015/0368625 A1 | 12/2015 | Segall-Shapiro et al. |
| 2016/0348096 A1* | 12/2016 | Liu .................... C40B 10/00 |

OTHER PUBLICATIONS

Dewey et al. Split T7 RNA polymerase biosensors to study multiprotein interaction dynamics. Epub Jun. 15, 2020. Methods of Enzymology. vol. 641, p. 413-432. (Year: 2020).*
Guntas et al. Engineering an improved light-induced dimer (iLID) for controlling the localization and activity of signaling proteins. Jan. 6, 2015. PNAS. vol. 112, No. 1, p. 112-117. (Year: 2015).*
Meinhardt et al. Rheostats and Toggle Switches for Modulating Protein Function. Dec. 30, 2013. PLOS One. vol. 8, Issue 12, e83502, pp. 1-11. (Year: 2013).*
Miller et al. Computational predictors fail to identify amino acid substitution effects at rheostat positions. Jan. 30, 2017. Scientific Reports. vol. 7, No. 41329, pp. 1-13. (Year: 2017).*
Pu et al. Evolution of a split RNA polymerase as a versatile biosensor platform. Feb. 13, 2017. Nature Chemical Biology. vol. 13, p. 432-438. (Year: 2017).*
Wehr and Rossner, Drug Discovery Today (2016), 21(3):415-429 (Year: 2016).*
BLAST alignments https://blast.ncbi.nlm.nih.gov/Blast.cgi [aligned Oct. 3, 2022] (Year: 2022).*
PTSara plasmid #60720 map and sequence, https://www.addgene.org/60720/ [retrieved Oct. 2, 2022] (Year: 2013).*
Veitia, Exploring the Molecular Etiology of Dominant-Negative Mutations. The Plant Cell (2007), 19:3843-3851 (Year: 2007).*
Slavoff et al., Imaging Protein-Protein Interactions inside Living Cells via Interaction-Dependent Fluorophore Ligation. JACS (2011), 133: 19769-19776 (Year: 2011).*
International Search Report and Written Opinion Issued in Corresponding PCT Application No. PCT/IB2017/053324, dated Jan. 29, 2018.
Pu, et al., "A Panel of Protease-Responsive RNA Polymerases Respond to Biochemical Signals by Production of Defined RNA Outputs in Live Cells," *Journal of the American Chem Society*, 137(51); 15996-15999, 2015.
Putz, et al., "A Tri-Hybiid System for the Analysis and Detection of RNA-Protein Interactions," *Nucleic Acids Research*, 24(23); 4838-4840, 1996.

(Continued)

*Primary Examiner* — Samuel C Woolwine
*Assistant Examiner* — Catherine Konopka
(74) *Attorney, Agent, or Firm* — Norton Rose Fulbright US LLP

(57) ABSTRACT

A proximity dependent split T7 RNAP (RNA polymerase) sensor using continuous molecular evolution is described. The versatility of the platform is described by creating robust light and small molecule-responsive genetic sensors. The activity-responsive RNAP platform dramatically simplifies and expands genetic circuit creation, and opens new opportunities in protein engineering, synthetic biology, and bioengineering.

13 Claims, 10 Drawing Sheets
Specification includes a Sequence Listing.

(56) References Cited

OTHER PUBLICATIONS

Segall-Shapiro, et al., "A Resource Allocator For Transcription Based on a Highly Fragmented T7 RNA Polymerase," *Molecular Systems Biology*, 10;742, 2014.
SenGupta, et al., "A Three-Hybrid System to Detect RNA-Protein Interactions In Vivo," *PNAS*, 93; 8496-8501, 1996.
Shekhawat, et al., "Split-Protein Systems: Beyond Binary Protein-Protein Interactions," *Current Opinion Chemical Biology*, 15(6); 789-797, 2011.
Shis, et al., "Library of Synthetic Transcriptional and Gates Built with Split T 7 RNA Polymerase Mutants," *PNAS*, 110(13); 5028-5033, 2013.

* cited by examiner

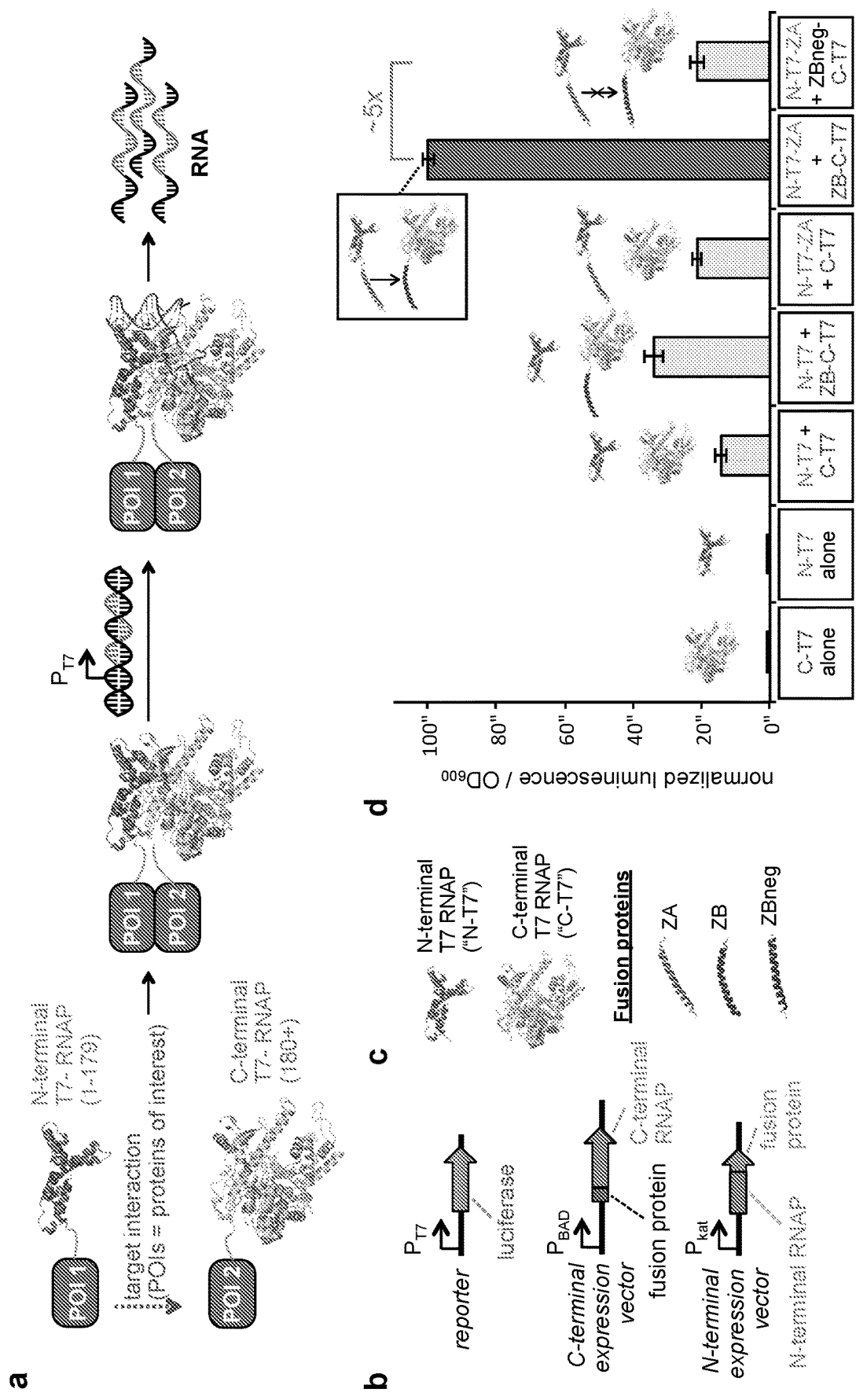
FIG. 1A-D

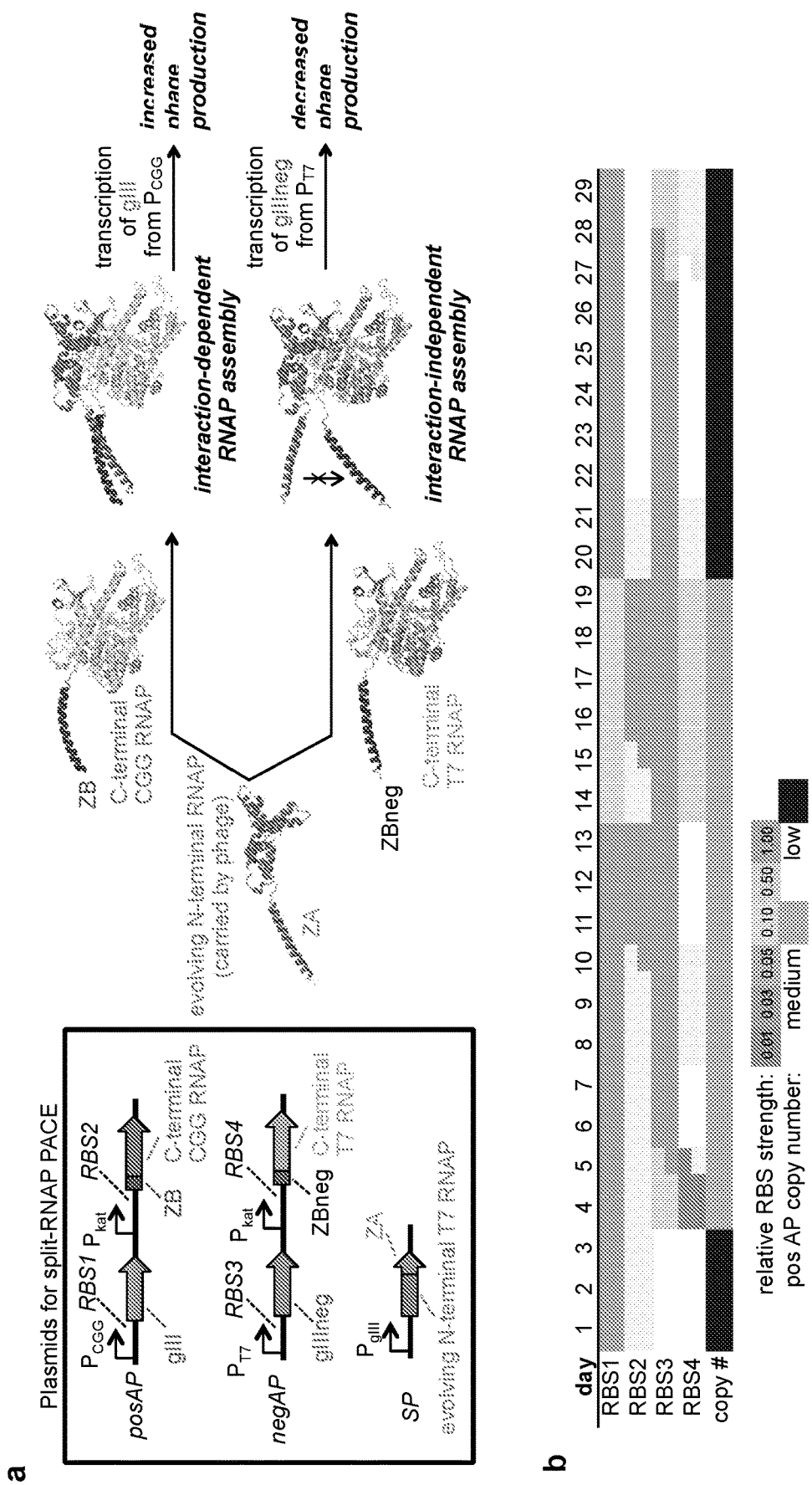
FIG. 2A-B

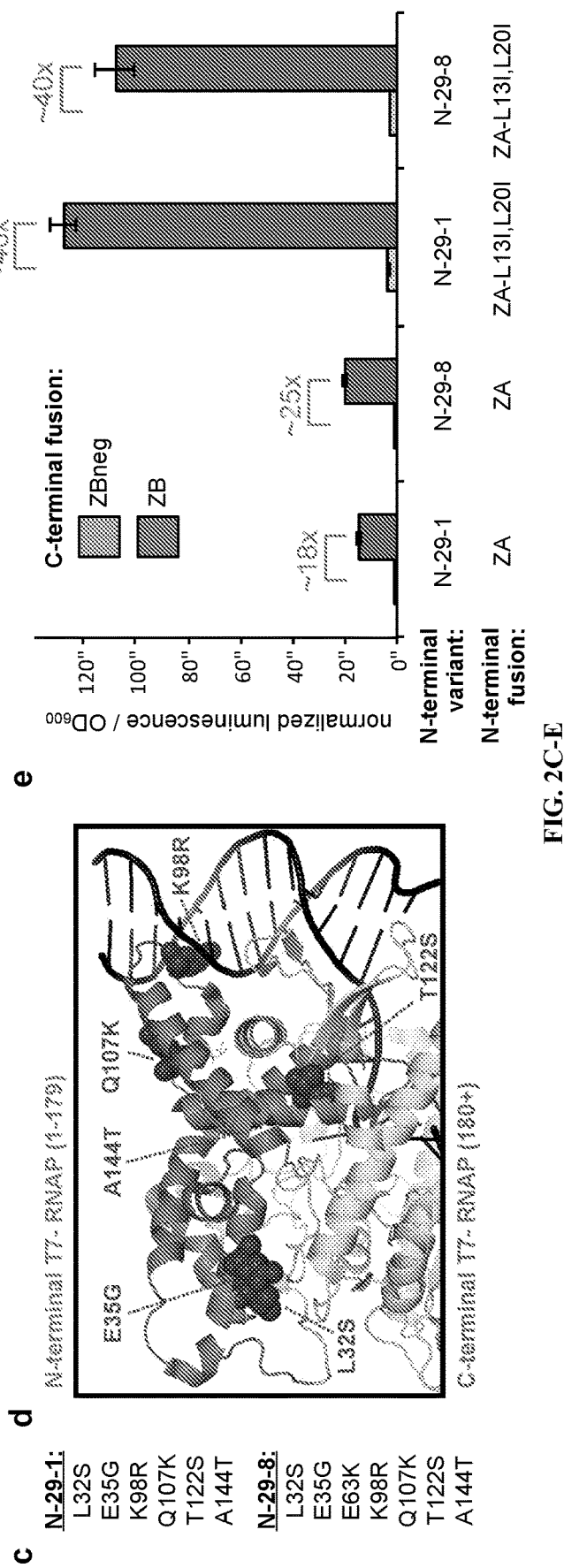
FIG. 2C-E

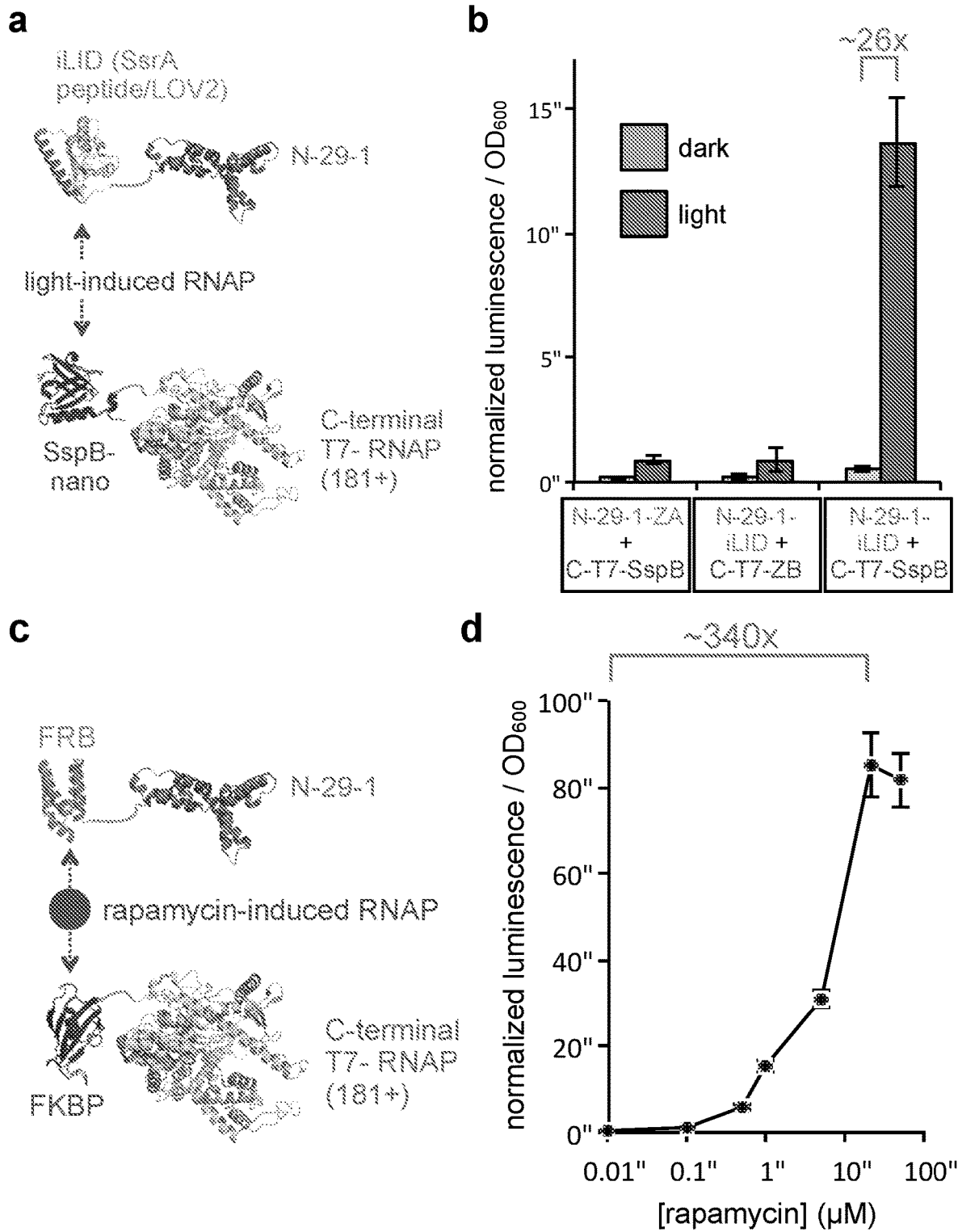
FIG. 3A-D

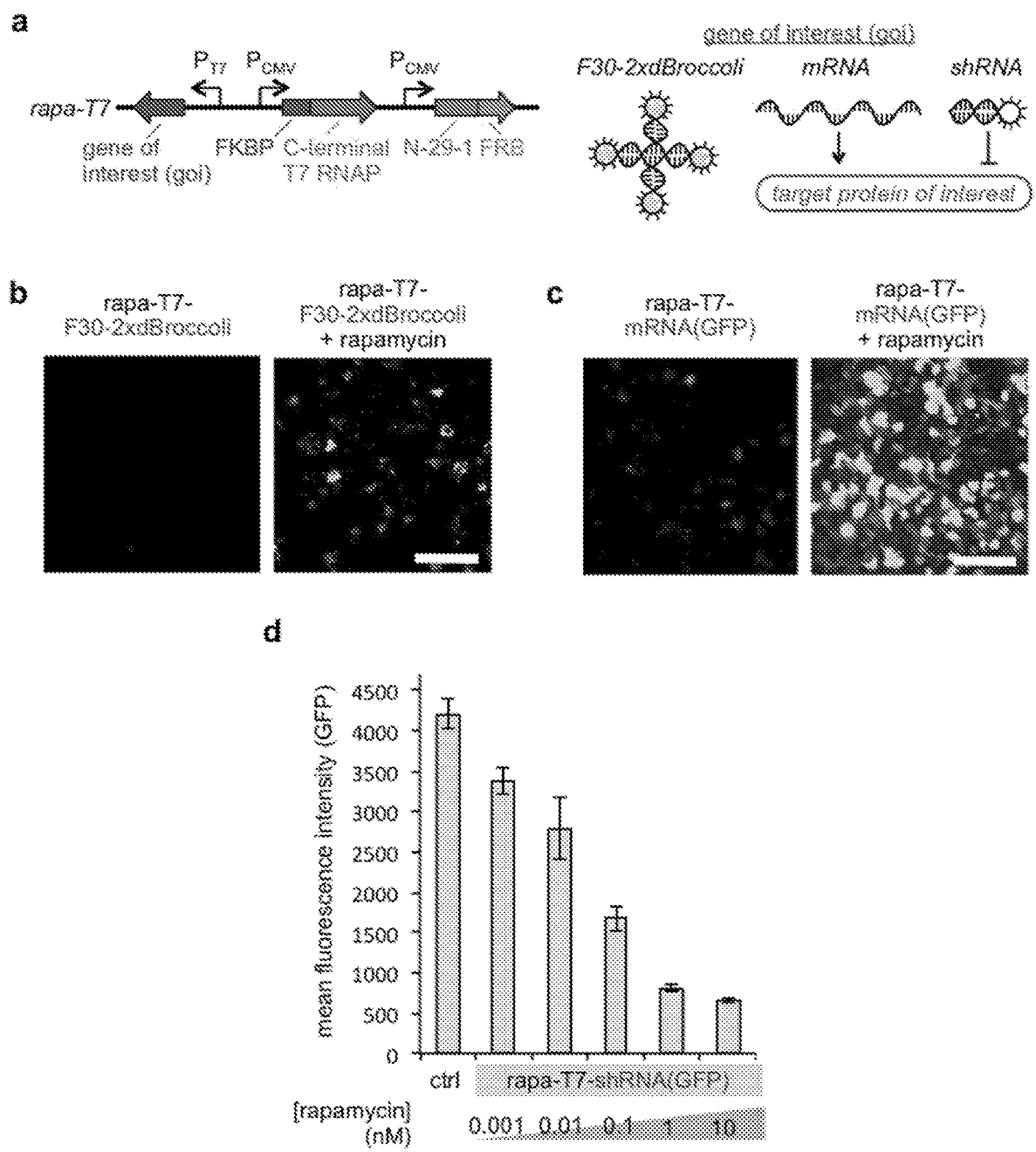
FIG. 4A-D

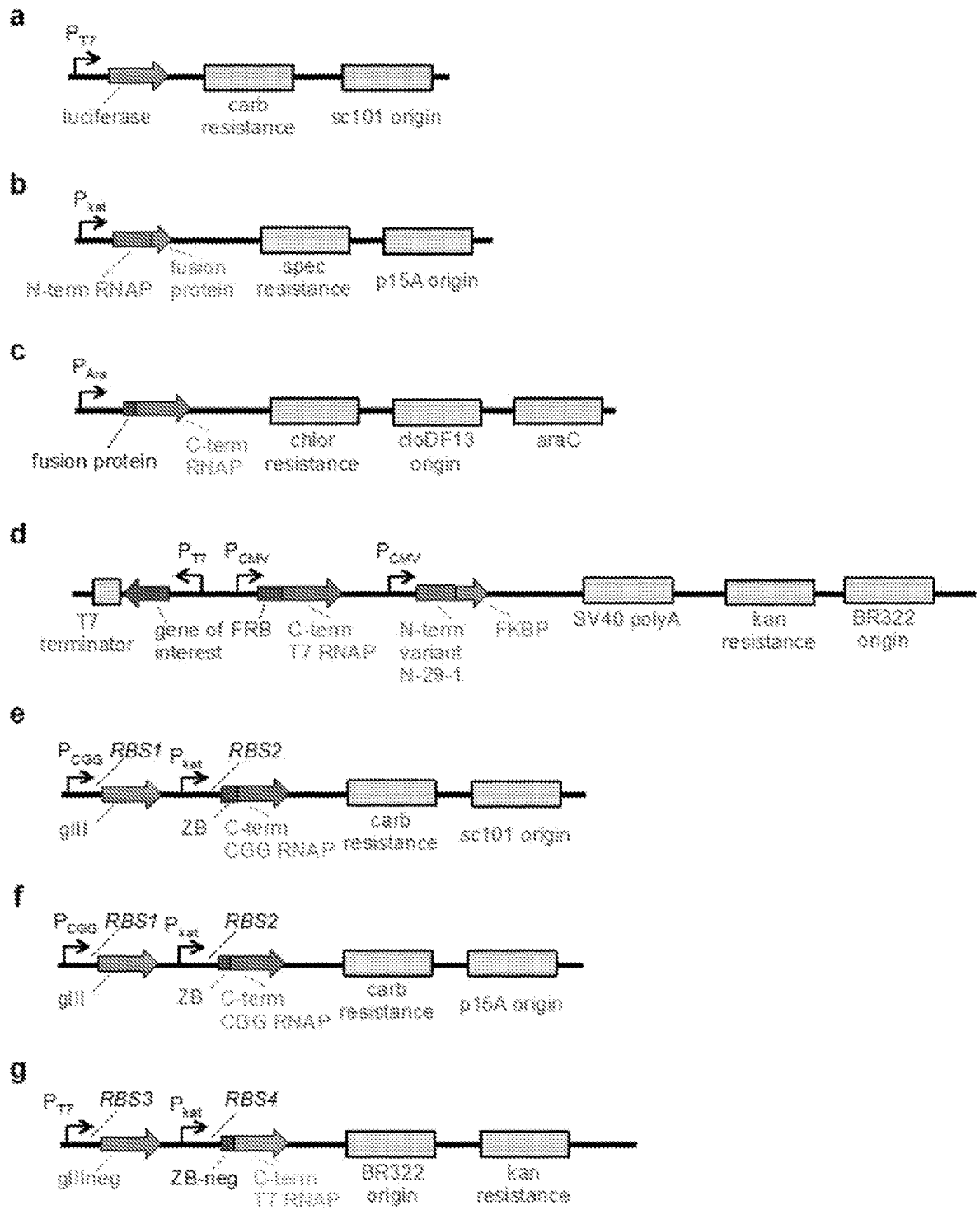
FIG. 5A-G

| evolutionary date | positive AP | | | | | negative AP | | | | |
|---|---|---|---|---|---|---|---|---|---|---|
| | Vector name | Map | origin | RBS1 | RBS2 | Vector name | Map | origin | RBS3 | RBS4 |
| day1 | Jin69 | e | sc101 | SD8 | sd8 | | | | | |
| day2 | Jin69 | e | sc101 | SD8 | sd8 | | | | | |
| day3 | Jin69 | e | sc101 | SD8 | sd8 | | | | | |
| day4 | Jin177 | f | p15A | SD8 | sd8 | Jin173 | g | pBR322 | SD4 | sd2 |
| | Jin177 | f | p15A | SD8 | sd8 | Jin173 | g | pBR322 | SD4 | sd2 |
| day5 | Jin177 | f | p15A | SD8 | sd8 | Jin172 | g | pBR322 | sd5 | sd6 |
| day6 | Jin177 | f | p15A | SD8 | sd8 | Jin172 | g | pBR322 | sd5 | sd6 |
| day7 | Jin177 | f | p15A | SD8 | sd8 | Jin172 | g | pBR322 | sd5 | sd6 |
| day8 | Jin177 | f | p15A | SD8 | sd8 | Jin104 | g | pBR322 | SD8 | sd8 |
| day9 | Jin177 | f | p15A | SD8 | sd8 | Jin104 | g | pBR322 | SD8 | sd8 |
| | Jin177 | f | p15A | SD8 | sd8 | Jin104 | g | pBR322 | SD8 | sd8 |
| day10 | Jin182 | f | p15A | sd5 | sd5 | Jin172 | g | pBR322 | sd5 | sd6 |
| day11 | Jin182 | f | p15A | sd5 | sd5 | Jin172 | g | pBR322 | sd5 | sd6 |
| day12 | Jin182 | f | p15A | sd5 | sd5 | Jin172 | g | pBR322 | sd5 | sd6 |
| day13 | Jin182 | f | p15A | sd5 | sd5 | Jin172 | g | pBR322 | sd5 | sd6 |
| day14 | Jin185 | f | p15A | SD4 | sd8 | Jin194 | g | pBR322 | SD8 | SD4 |
| | Jin185 | f | p15A | SD4 | sd8 | Jin194 | g | pBR322 | SD8 | SD4 |
| day15 | Jin196 | f | p15A | SD4 | sd5 | Jin194 | g | pBR322 | SD8 | SD4 |
| day16 | Jin196 | f | p15A | SD4 | sd5 | Jin194 | g | pBR322 | SD8 | SD4 |
| day17 | Jin196 | f | p15A | SD4 | sd5 | Jin194 | g | pBR322 | SD8 | SD4 |
| day18 | Jin196 | f | p15A | SD4 | sd5 | Jin194 | g | pBR322 | SD8 | SD4 |
| day19 | Jin196 | f | p15A | SD4 | sd5 | Jin194 | g | pBR322 | SD8 | SD4 |
| day20 | Jin70 | e | sc101 | SD8 | sd8 | Jin104 | g | pBR322 | SD8 | sd8 |
| day21 | Jin70 | e | sc101 | SD8 | sd8 | Jin104 | g | pBR322 | SD8 | sd8 |
| day22 | Jin178 | e | sc101 | SD8 | sd6 | Jin172 | g | pBR322 | sd5 | sd6 |
| day23 | Jin178 | e | sc101 | SD8 | sd6 | Jin172 | g | pBR322 | sd5 | sd6 |
| day24 | Jin178 | e | sc101 | SD8 | sd6 | Jin172 | g | pBR322 | sd5 | sd6 |
| day25 | Jin178 | e | sc101 | SD8 | sd6 | Jin172 | g | pBR322 | sd5 | sd6 |
| day26 | Jin178 | e | sc101 | SD8 | sd6 | Jin172 | g | pBR322 | sd5 | sd6 |
| | Jin178 | e | sc101 | SD8 | sd6 | Jin172 | g | pBR322 | sd5 | sd6 |
| day27 | Jin178 | e | sc101 | SD8 | sd6 | Jin172 | g | pBR322 | sd5 | sd6 |
| | Jin178 | e | sc101 | SD8 | sd6 | Jin171 | g | pBR322 | SD4 | sd8 |
| day28 | Jin178 | e | sc101 | SD8 | sd6 | Jin171 | g | pBR322 | SD4 | sd8 |
| day29 | Jin178 | e | sc101 | SD8 | sd6 | Jin171 | g | pBR322 | SD4 | sd8 |

FIG. 6

| day 3 | | | | | | | | |
|---|---|---|---|---|---|---|---|---|
| N-3-1 | | | | | | | | |
| N-3-2 | | | | | | | | |
| N-3-3 | | | D87N | | | | | |
| N-3-4 | D26Y | | | | | | | |
| N-3-5 | | | | | S120N | | | |
| N-3-6 | | | | | | | | |
| N-3-7 | | | | | | | | |
| N-3-8 | | | | | | | | |
| day 7 | | | | | | | | |
| N-7-1 | | L32S | E63K | | | K98R Q107K | | |
| N-7-2 | | L32S | E63K | | | K98R Q107K | | |
| N-7-3 | | L32S | | | | K98R Q107K I109T | | |
| N-7-4 | | | | | | K98R Q107K | | |
| N-7-5 | | | E63K | | | K98R Q107K | | |
| N-7-6 | | L32S | | | E91G | K98R Q107K | | |
| N-7-7 | | L32S | E63K | | | K98R Q107K | | |
| N-7-8 | E25Q | L32S | | | E91G | K98R Q107K | | |
| day 8 | | | | | | | | |
| N-8-1 | | L32S | E63K | | E91G | K98R Q107K | | |
| N-8-2 | | L32S | E63K | | | K98R Q107K | | |
| N-8-3 | | | E63K | | | K98R Q107K I109T | | |
| N-8-4 | | L32S | | | | K98R Q107K | | |
| N-8-5 | | | E63K | | | K98R Q107K | | |
| N-8-6 | | | E63K | | | K98R Q107K | | |
| N-8-7 | | L32S E35D | | | E91G | K98R Q107K | | G152D |
| N-8-8 | | L32S | E63K | | | K98R Q107K | | |

FIG. 7A

FIG. 7B day 13
- N-13-1: L32S, E35G, E91G, K98R, Q107K, A144T
- N-13-2: L32S, E35G, E63K, K98R, Q107K
- N-13-3: D26G, E63K, K98R, Q107K, A159S
- N-13-4: L32S, E35G, E91G, K98R, Q107K, A144T
- N-13-5: L32S, E35G, E91G, K98R, Q107K
- N-13-6: L32S, E35G, E91G, K98R, Q107K day 21
- N-21-1: L32S, E35G, E91G, K98R, Q107K
- N-21-2: L32S, E35G, E91G, K98R, Q107K, A149T
- N-21-3: L32S, E35G, E91G, K98R, Q107K
- N-21-4: L32S, E35G, A49S, E91G, K98R, Q107K, A149T
- N-21-5: L32S, E35G, E91G, K98R, A124S
- N-21-6: L32S, E35G, E91G, K98R, Q107K
- N-21-7: L32S, E35G, A83T, E91G, K98R, Q107K
- N-21-8: L32S, E35G, A83T, E91G, K98R, Q107K
- N-21-9: L32S, E35G, A83T, E91G, K98R, Q107K
- N-21-10: L32S, E35G, E63K, D87E, K98R, Q107K, T122S, A144T

| | | | | | | | | |
|---|---|---|---|---|---|---|---|---|
| day27 | | | | | | | | |
| N-27-1 | | | | | | | | |
| N-27-2 | | | | | | | | |
| N-27-3 | L32S | E35G | | | K98R | | | |
| N-27-4 | L32S | E35G | | E91G | K98R Q107K | A124S | | |
| N-27-5 | L32S | E35G | E63K | E91G | K98R Q107K | A124S | | |
| N-27-6 | L32S | E35G | E63K | | K98R Q107K T122S | | | A144T |
| N-27-7 | L32S | E35G | E63K | | K98R Q107K T122S | | | A144T |
| N-27-8 | L32S | E35G | E63K | N86S | Q107K T122S | | | A144T |
| | | | | | Q107K T122S | | | A144T |
| day29 | | | | | | | | |
| N-29-1 | L32S | E35G | | | K98R Q107K T122S | | | A144T |
| N-29-2 | L32S | E35G | | | K98R Q107K T122S | | T127A | A136D A144T |
| N-29-3 | L32S | E35G | E63K | | K98R Q107K T122S | | | A144T |
| N-29-4 | L32S | E35G | E63K | | K98R Q107K T122S | | | A144T |
| N-29-5 | L32S | E35G | E63K | | K98R Q107K T122S | | | A144T |
| N-29-6 | L32S | E35G | E63K | | K98R Q107K T122S | | | A144T |
| N-29-8 | L32S | E35G | E63K | | K98R Q107K T122S | | | A144T |

FIG. 7C

SEQUENCE LISTING

```
<160> NUMBER OF SEQ ID NOS: 16

<210> SEQ ID NO 1
<211> LENGTH: 2115
<212> TYPE: DNA
<213> ORGANISM: Artificial Sequence
<220> FEATURE:
<223> OTHER INFORMATION: Synthetic Nucleic Acid

<400> SEQUENCE: 1
aaagcattta tgcaagttgt cgaggctgac atgctctcta agggtctact cggtggcgag      60
gcgtggtctt cgtggcataa ggaagactct attcatgtag gagtacgctg catcgagatg     120
ctcattgagt caaccggaat ggttagctta caccgccaaa atgctggcgt agtaggtcaa     180
```

```
gactctgaga ctatcgaact cgcacctgaa tacgctgagg ctatcgcaac ccgtgcaggt    240
gcgctggctg gcatctctcc gatgttccaa ccttgcgtag ttcctcctaa gccgtggact    300
ggcattactg gtggtggcta ttgggctaac ggtcgtcgtc ctctggcgct ggtgcgtact    360
cacagtaaga aagcactgat gcgctacgaa gacgtttaca tgcctgaggt gtacaaagcg    420
attaacattg cgcaaaacac cgcatggaaa atcaacaaga aagtcctagc ggtcgccaac    480
gtaatcacca gtggaagca ttgtccggtc gaggacatcc ctgcgattga gcgtgaagaa    540
ctcccgatga aaccggaaga catcgacatg aatcctgagg ctctcaccgc gtggaaacgt    600
gctgccgctg ctgtgtaccg caaggacaag gctcgcaagt ctcgccgtat cagccttgag    660
ttcatgcttg agcaagccaa taagtttgct aaccataagg ccatctggtt cccttacaac    720
atggactggc gcgtcgtgt ttacgctgtg tcaatgttca acccgcaagg taacgatatg    780
accaaaggac tgcttacgct ggcgaaaggt aaaccaatcg gtaaggaagg ttactactgg    840
ctgaaaatcc acggtgcaaa ctgtgcgggt gtcgataagg ttccgttccc tgagcgcatc    900
aagttcattg aggaaaacca cgagaacatc atggcttgcg ctaagtctcc actggagaac    960
acttggtggg ctgagcaaga ttctccgttc tgcttccttg cgttctgctt tgagtacgct   1020
ggggtacagc accacggcct gagctataac tgctccttc cgctggcgtt tgacgggtct   1080
tgctctggca tccagcactt ctccgcgatg ctccgagatg aggtaggtgg tcgcgcggtt   1140
aacttgcttc ctagtgaaac cgttcaggac atctacggga ttgttgctaa gaaagtcaac   1200
gagattctac aagcagacgc aatcaatggg accgataacg aagtagttac cgtgaccgat   1260
gagaacactg gtgaaatctc tgagaaagtc aagctgggca ctaaggcact ggctggtcaa   1320
tggctggctt acggtgttac tcgcagtgtg actaagcgtt cagtcatgac gctggcttac   1380
gggtccaaag agttcggctt ccgtcaacaa gtgctggaag ataccattca gccagctatt   1440
gattccggca agggtctgat gttcactcag ccgaatcagg ctgctggata catggctaag   1500
ctgatttggg aatctgtgag cgtgacggtg gtagctgcgg ttgaagcaat gaactggctt   1560
aagtctgctg ctaagctgct ggctgctgag gtcaaagata agaagactgg agagattctt   1620
cgcaagcgtt gcgctgtgca ttgggtaact cctgatggtt tccctgtgtg gcaggaatac   1680
aagaagccta ttcagacgcg cttgaacctg atgttcctcg gtcagttccg cttacagcct   1740
accattaaca ccaacaaaga tagcgagatt gatgcacaca acaggagtc tggtatcgct   1800
cctaactttg tacacagcca agacggtagc caccttcgta agactgtagt gtgggcacac   1860
gagaagtacg gaatcgaatc ttttgcactg attcacgact ccttcggtac cattccggct   1920
gacgctgcga acctgttcaa agcagtgcgc gaaactatgg ttgacacata tgagtcttgt   1980
gatgtactgc tgatttcta cgaccagttc gctgaccagt tgcacgagtc tcaattggac   2040
aaaatgccag cacttccggc taaaggtaac ttgaacctcc gtgacatctt agagtcggac   2100
ttcgcgttcg cgtaa                                                    2115
```

<210> SEQ ID NO 2
<211> LENGTH: 704
<212> TYPE: PRT
<213> ORGANISM: Artificial Sequence
<220> FEATURE:
<223> OTHER INFORMATION: Synthetic Polypeptide

<400> SEQUENCE: 2

Lys Ala Phe Met Gln Val Val Glu Ala Asp Met Leu Ser Lys Gly Leu
1               5                   10                  15

Leu Gly Gly Glu Ala Trp Ser Ser Trp His Lys Glu Asp Ser Ile His
            20                  25                  30

Val Gly Val Arg Cys Ile Glu Met Leu Ile Glu Ser Thr Gly Met Val
            35                  40                  45

Ser Leu His Arg Gln Asn Ala Gly Val Val Gly Gln Asp Ser Glu Thr
    50                  55                  60

Ile Glu Leu Ala Pro Glu Tyr Ala Glu Ala Ile Ala Thr Arg Ala Gly
65                  70                  75                  80

Ala Leu Ala Gly Ile Ser Pro Met Phe Gln Pro Cys Val Val Pro Pro
                85                  90                  95

Lys Pro Trp Thr Gly Ile Thr Gly Gly Tyr Trp Ala Asn Gly Arg
            100                 105                 110

Arg Pro Leu Ala Leu Val Arg Thr His Ser Lys Lys Ala Leu Met Arg
        115                 120                 125

Tyr Glu Asp Val Tyr Met Pro Glu Val Tyr Lys Ala Ile Asn Ile Ala
130                 135                 140

Gln Asn Thr Ala Trp Lys Ile Asn Lys Lys Val Leu Ala Val Ala Asn
145                 150                 155                 160

Val Ile Thr Lys Trp Lys His Cys Pro Val Glu Asp Ile Pro Ala Ile
                165                 170                 175

Glu Arg Glu Glu Leu Pro Met Lys Pro Glu Asp Ile Asp Met Asn Pro
            180                 185                 190

Glu Ala Leu Thr Ala Trp Lys Arg Ala Ala Ala Val Tyr Arg Lys
        195                 200                 205

Asp Lys Ala Arg Lys Ser Arg Arg Ile Ser Leu Glu Phe Met Leu Glu
210                 215                 220

Gln Ala Asn Lys Phe Ala Asn His Lys Ala Ile Trp Phe Pro Tyr Asn
225                 230                 235                 240

Met Asp Trp Arg Gly Arg Val Tyr Ala Val Ser Met Phe Asn Pro Gln
                245                 250                 255

Gly Asn Asp Met Thr Lys Gly Leu Leu Thr Leu Ala Lys Gly Lys Pro
            260                 265                 270

Ile Gly Lys Glu Gly Tyr Tyr Trp Leu Lys Ile His Gly Ala Asn Cys
        275                 280                 285

Ala Gly Val Asp Lys Val Pro Phe Pro Glu Arg Ile Lys Phe Ile Glu
290                 295                 300

Glu Asn His Glu Asn Ile Met Ala Cys Ala Lys Ser Pro Leu Glu Asn
305                 310                 315                 320

Thr Trp Trp Ala Glu Gln Asp Ser Pro Phe Cys Phe Leu Ala Phe Cys
                325                 330                 335

Phe Glu Tyr Ala Gly Val Gln His His Gly Leu Ser Tyr Asn Cys Ser
            340                 345                 350

Leu Pro Leu Ala Phe Asp Gly Ser Cys Ser Gly Ile Gln His Phe Ser
        355                 360                 365

Ala Met Leu Arg Asp Glu Val Gly Gly Arg Ala Val Asn Leu Leu Pro
370                 375                 380

Ser Glu Thr Val Gln Asp Ile Tyr Gly Ile Val Ala Lys Lys Val Asn
385                 390                 395                 400

Glu Ile Leu Gln Ala Asp Ala Ile Asn Gly Thr Asp Asn Glu Val Val
                405                 410                 415

Thr Val Thr Asp Glu Asn Thr Gly Glu Ile Ser Glu Lys Val Lys Leu
            420                 425                 430

Gly Thr Lys Ala Leu Ala Gly Gln Trp Leu Ala Tyr Gly Val Thr Arg
            435                 440                 445

Ser Val Thr Lys Arg Ser Val Met Thr Leu Ala Tyr Gly Ser Lys Glu
        450                 455                 460

Phe Gly Phe Arg Gln Gln Val Leu Glu Asp Thr Ile Gln Pro Ala Ile
465                 470                 475                 480

Asp Ser Gly Lys Gly Leu Met Phe Thr Gln Pro Asn Gln Ala Ala Gly
                485                 490                 495

Tyr Met Ala Lys Leu Ile Trp Glu Ser Val Ser Val Thr Val Val Ala
            500                 505                 510

Ala Val Glu Ala Met Asn Trp Leu Lys Ser Ala Ala Lys Leu Leu Ala
        515                 520                 525

Ala Glu Val Lys Asp Lys Lys Thr Gly Glu Ile Leu Arg Lys Arg Cys
530                 535                 540

Ala Val His Trp Val Thr Pro Asp Gly Phe Pro Val Trp Gln Glu Tyr
545                 550                 555                 560

Lys Lys Pro Ile Gln Thr Arg Leu Asn Leu Met Phe Leu Gly Gln Phe
                565                 570                 575

Arg Leu Gln Pro Thr Ile Asn Thr Asn Lys Asp Ser Glu Ile Asp Ala
            580                 585                 590

His Lys Gln Glu Ser Gly Ile Ala Pro Asn Phe Val His Ser Gln Asp
        595                 600                 605

Gly Ser His Leu Arg Lys Thr Val Val Trp Ala His Glu Lys Tyr Gly
        610                 615                 620

Ile Glu Ser Phe Ala Leu Ile His Asp Ser Phe Gly Thr Ile Pro Ala
625                 630                 635                 640

Asp Ala Ala Asn Leu Phe Lys Ala Val Arg Glu Thr Met Val Asp Thr
                645                 650                 655

Tyr Glu Ser Cys Asp Val Leu Ala Asp Phe Tyr Asp Gln Phe Ala Asp
            660                 665                 670

Gln Leu His Glu Ser Gln Leu Asp Lys Met Pro Ala Leu Pro Ala Lys
        675                 680                 685

Gly Asn Leu Asn Leu Arg Asp Ile Leu Glu Ser Asp Phe Ala Phe Ala
690                 695                 700

<210> SEQ ID NO 3
<211> LENGTH: 537
<212> TYPE: DNA
<213> ORGANISM: Artificial Sequence
<220> FEATURE:
<223> OTHER INFORMATION: Synthetic Nucleic Acid

<400> SEQUENCE: 3
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta ccgtgacct tgaagctaag    480 cacttcaaga aaacgttga ggaacaactc aacaagcgcg tagggcacgt ctacaag       537

<210> SEQ ID NO 4
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 4

```
Met Asn Thr Ile Asn Ile Ala Lys Asn Asp Phe Ser Asp Ile Glu Leu
 1               5                  10                  15

Ala Ala Ile Pro Phe Asn Thr Leu Ala Asp His Tyr Gly Glu Arg Leu
             20                  25                  30

Ala Arg Glu Gln Leu Ala Leu Glu His Glu Ser Tyr Glu Met Gly Glu
         35                  40                  45

Ala Arg Phe Arg Lys Met Phe Glu Arg Gln Leu Lys Ala Gly Glu Val
     50                  55                  60

Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys
```

<210> SEQ ID NO 5
<211> LENGTH: 537
<212> TYPE: DNA
<213> ORGANISM: Artificial Sequence
<220> FEATURE:
<223> OTHER INFORMATION: Synthetic Nucleic Acid

<400> SEQUENCE: 5

```
atgaacacga ttaacatcgc taagaacgac ttctctgaca tcgaactggc tgctatcccg      60
ttcaacactc tggctgacca ttacggtgag cgttcagctc gcggacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgccc gcatcaacga ctggtttgag gaagtgaaag ctaagcgcgg caggcgcccg     300
acagccttcc agttcctaaa agaaatcaag ccggaagccg tagcgtacat caccattaag     360
acctctctgg cttgcctaac cagtgctgac aatacaaccg ttcaggctgt agcaagcgca     420
atcggtcgga ccattgagga cgaggctcgc ttcggtcgta ccgtgacct tgaagctaag     480
cacttcaaga aaacgttga ggaacaactc aacaagcgcg tagggcacgt ctacaag        537
```

<210> SEQ ID NO 6
<211> LENGTH: 179
<212> TYPE: PRT
<213> ORGANISM: Artificial Sequence
<220> FEATURE:

<223> OTHER INFORMATION: Synthetic Polypeptide

<400> SEQUENCE: 6

Met Asn Thr Ile Asn Ile Ala Lys Asn Asp Phe Ser Asp Ile Glu Leu
1               5                   10                  15
Ala Ala Ile Pro Phe Asn Thr Leu Ala Asp His Tyr Gly Glu Arg Ser
            20                  25                  30
Ala Arg Gly Gln Leu Ala Leu Glu His Glu Ser Tyr Glu Met Gly Glu
        35                  40                  45
Ala Arg Phe Arg Lys Met Phe Glu Arg Gln Leu Lys Ala Gly Glu Val
    50                  55                  60
Ala Asp Asn Ala Ala Ala Lys Pro Leu Ile Thr Thr Leu Leu Pro Lys
65                  70                  75                  80
Met Ile Ala Arg Ile Asn Asp Trp Phe Glu Glu Val Lys Ala Lys Arg
                85                  90                  95
Gly Arg Arg Pro Thr Ala Phe Gln Phe Leu Lys Glu Ile Lys Pro Glu
            100                 105                 110
Ala Val Ala Tyr Ile Thr Ile Lys Thr Ser Leu Ala Cys Leu Thr Ser
        115                 120                 125
Ala Asp Asn Thr Thr Val Gln Ala Val Ala Ser Ala Ile Gly Arg Thr
    130                 135                 140
Ile Glu Asp Glu Ala Arg Phe Gly Arg Ile Arg Asp Leu Glu Ala Lys
145                 150                 155                 160
His Phe Lys Lys Asn Val Glu Glu Gln Leu Asn Lys Arg Val Gly His
                165                 170                 175
Val Tyr Lys

<210> SEQ ID NO 7
<211> LENGTH: 537
<212> TYPE: DNA
<213> ORGANISM: Artificial Sequence
<220> FEATURE:
<223> OTHER INFORMATION: Synthetic Nucleic Acid

<400> SEQUENCE: 7
atgaacacga ttaacatcgc taagaacgac ttctctgaca tcgaactggc tgctatcccg      60
ttcaacactc tggctgacca ttacggtgag cgttcagctc gcggacagtt ggcccttgag     120
catgagtctt acgagatggg tgaagcacgc ttccgcaaga tgtttgagcg tcaacttaaa     180
gctggtaagg ttgcggataa cgctgccgcc aagcctctca tcactaccct actccctaag     240
atgattgccc gcatcaacga ctggtttgag gaagtgaaag ctaagcgcgg caggcgcccg     300
acagccttcc agttcctaaa agaaatcaag ccggaagccg tagcgtacat caccattaag     360
acctctctgg cttgcctaac cagtgctgac aatacaaccg ttcaggctgt agcaagcgca     420
atcggtcgga ccattgagga cgaggctcgc ttcggtcgta tccgtgacct tgaagctaag     480
cacttcaaga aaaacgttga ggaacaactc aacaagcgcg tagggcacgt ctacaag       537

<210> SEQ ID NO 8
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 8

Met Asn Thr Ile Asn Ile Ala Lys Asn Asp Phe Ser Asp Ile Glu Leu
1               5                   10                  15

-continued

```
Ala Ala Ile Pro Phe Asn Thr Leu Ala Asp His Tyr Gly Glu Arg Ser
            20                  25                  30

Ala Arg Gly Gln Leu Ala Leu Glu His Glu Ser Tyr Glu Met Gly Glu
        35                  40                  45

Ala Arg Phe Arg Lys Met Phe Glu Arg Gln Leu Lys Ala Gly Lys Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Arg Arg Pro Thr Ala Phe Gln Phe Leu Lys Glu Ile Lys Pro Glu
            100                 105                 110

Ala Val Ala Tyr Ile Thr Ile Lys Thr Ser Leu Ala Cys Leu Thr Ser
        115                 120                 125

Ala Asp Asn Thr Thr Val Gln Ala Val Ala Ser Ala Ile Gly Arg Thr
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys

<210> SEQ ID NO 9
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: RNAP(1-179) tagged

<400> SEQUENCE: 9

Gly Gly Ser Gly Ser Gly Ser Ser Ala Leu Lys Lys Glu Leu Gln Ala
1               5                   10                  15

Asn Lys Lys Glu Leu Ala Gln Leu Lys Trp Glu Leu Gln Ala Leu Lys
            20                  25                  30

Lys Glu Leu Ala Gln
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (39)..(39)
<223> OTHER INFORMATION: RNAP(180+) tagged

<400> SEQUENCE: 10

Met Ala Ser Glu Gln Leu Glu Lys Lys Leu Gln Ala Leu Glu Lys Lys
1               5                   10                  15

Leu Ala Gln Leu Glu Trp Lys Asn Gln Ala Leu Glu Lys Lys Leu Ala
            20                  25                  30

Gln Thr Ser Gly Gly Ser Gly
        35
```

<210> SEQ ID NO 11
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (39)..(39)
<223> OTHER INFORMATION: RNAP(180+) tagged

<400> SEQUENCE: 11

Met Ala Ser Glu Gln Leu Glu Lys Glu Leu Gln Ala Leu Glu Lys Glu
1               5                   10                  15

Leu Ala Gln Leu Lys Trp Lys Asn Gln Ala Leu Glu Lys Lys Leu Ala
            20                  25                  30

Gln Thr Ser Gly Gly Ser Gly
        35

<210> SEQ ID NO 12
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-28-1(1-179) tagged

<400> SEQUENCE: 12

Gly Gly Ser Gly Ser Gly Ser Ser Ala Leu Lys Lys Glu Leu Gln Ala
1               5                   10                  15

Asn Lys Lys Glu Ile Ala Gln Leu Lys Trp Glu Ile Gln Ala Leu Lys
            20                  25                  30

Lys Glu Leu Ala Gln
        35

<210> SEQ ID NO 13
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-28-1(1-179) tagged
<220> FEATURE:
<221> NAME/KEY: MISC_FEATURE
<222> LOCATION: (8)..(8)
<223> OTHER INFORMATION: iLID tagged

<400> SEQUENCE: 13

Gly Gly Ser Gly Ser Gly Ser Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: SspBnano tagged
<220> FEATURE:

```
<221> NAME/KEY: MISC_FEATURE
<222> LOCATION: (6)..(6)
<223> OTHER INFORMATION: RNAP(180+) tagged

<400> SEQUENCE: 14

Thr Ser Gly Gly Ser Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-28-1(1-179) tagged
<220> FEATURE:
<221> NAME/KEY: MISC_FEATURE
<222> LOCATION: (8)..(8)
<223> OTHER INFORMATION: FRB tagged

<400> SEQUENCE: 15

Gly Gly Ser Gly Ser Gly Ser Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: FKBP tagged
<220> FEATURE:
<221> NAME/KEY: MISC_FEATURE
<222> LOCATION: (6)..(6)
<223> OTHER INFORMATION: RNAP(180+) tagged

<400> SEQUENCE: 16

Thr Ser Gly Gly Ser Gly
1               5
```

PROXIMITY-DEPENDENT SPLIT RNA POLYMERASES AS A VERSATILE BIOSENSOR PLATFORM

CROSS-REFERENCE TO RELATED APPLICATIONS

This application is a national phase application under 35 U.S.C. § 371 of International Application No. PCT/IB2017/053324 filed Jun. 6, 2017, which claims the benefit of priority of U.S. Provisional Patent Application No. 62/346,174 filed Jun. 6, 2016, and U.S. Provisional Patent Application No. 62/424,875 filed Nov. 21, 2016. The entire contents of each of the above-referenced disclosures are specifically incorporated herein by reference without disclaimer.

STATEMENT OF GOVERNMENT RIGHTS

This invention was made with government support under grant number CA014599 awarded by the National Institutes of Health. The government has certain rights in the invention.

BACKGROUND OF THE INVENTION

1. Field of the Invention

The present invention relates generally to the field of chemistry and medicine. More particularly, it concerns the use of a split RNA polymerase as a versatile biosensor platform.

2. Description of Related Art

Biosensors that transduce target chemical and biochemical inputs into genetic outputs are essential for bioengineering and synthetic biology. Current approaches, such as "n-hybrid" and aptamer-based systems, often suffer from a lack of signal-to-noise, requirements for extensive optimization for each new input, and poor performance in mammalian cells.

SUMMARY OF THE INVENTION

Methods, systems, compositions, and kits are provided that involve engineered nucleic acids, engineered polypeptides, engineered cells, and/or engineered organisms for screening, identifying and optimizing cellular interactions involving nucleic acids, polypeptides, cells, and/or organisms. In particular embodiments, methods, systems, compositions, and kits involve truncated polymerase portions or domains that do not have polymerase activity unless the portions or domains are in proximity with one another. One or more components can be attached to each portion or domain such that an interaction between one or more components can qualified and/or quantitated based on polymerase activity. Transcription is one way in which the interaction can be evaluated using a promoter responsive to the polymerase activity. The term polymerase activity is used according to its common scientific meaning, which is the activity of synthesizing DNA or RNA.

Among other advantages, the methods, systems, compositions and kits provide improved biosensing resulting from an improved polymerase combination such as an engineered polymerase system. The polymerase combination involves a polymerase that has been separated into at least two parts such that a part of a polymerase is a "polymerase domain." One part comprises a polymerase domain that comprises an N-terminal portion of the polymerase while the other part comprises a polymerase domain that comprises a C-terminal portion of the same polymerase or different but related polymerase. Engineered polymerase domains that do not have polymerase activity on their own but that have polymerase activity when they come together constitute an engineered polymerase system. In certain embodiments, the polymerase is split into two equal or unequal parts such that one part comprises an N-terminal portion and the other part comprises the C-terminal portion of the same polymerase. While it is contemplated that in some embodiments the two parts provide the full length polymerase (which may or may not have amino acid substitutions relative to a wild-type or already existing recombinant polymerase), in other embodiments, the two parts may not provide the full-length polymerase as one or both parts may have additional truncations at either end or have one or more internal deletions within a part.

In specific embodiments, the methods, systems, compositions and kits involve an N-terminal polymerase domain and a C-terminal polymerase domain each of which is attached or connected to either a target or an interaction component. The term "N-terminal polymerase domain" refers to a less-than full length portion of a polymerase in a polymerase combination system that comprises the N-terminal portion of a polymerase relative to the C-terminal portion or "C-terminal polymerase domain" of the same polymerase or a related polymerase. A polymerase domain may be attached to one target while another polymerase domain in an engineered polymerase system or polymerase combination may be attached to a different target. Similarly, a polymerase domain may be attached to one interaction component while another polymerase domain in an engineered polymerase system or polymerase combination may be attached to a different interaction component. In some embodiments, the different targets are capable of physically and/or chemically interacting with one another. The term "interaction component" refers to a chemical moiety or entity that is capable of physically and/or chemically interacting with another interaction component. In specific embodiments, the interaction components are polypeptides (and/or peptides) that specifically bind one another or a polypeptide and a nucleic acid that specifically bind one another or nucleic acids that specifically bind one another or a polypeptide that specifically binds a small molecule that is not a nucleic acid or a polypeptide or peptide. An example is an antigen and antibody CDRs (in a single chain, for instance) that specifically bind one another. Other examples include, but are not limited to, a receptor and a ligand. It is specifically contemplated that a target or interaction component may be or comprise a peptide, a polypeptide, a nucleic acid, or a small molecule. Embodiments concern an N-terminal polymerase domain or a C-terminal polymerase domain that is connected to either a target or an interaction component; these engineered polypeptides are chimeric and they do not occur in nature.

In some embodiments, there is a system or kit comprising one or more of the following components: a polymerase domain attached to an interaction component; a first polymerase domain attached to a first interaction component; a second polymerase domain attached to a second interaction component; a nucleic acid construct comprising a reporter gene; a nucleic acid comprising a promoter responsive to an engineered polymerase or engineered polymerase system, a candidate compound, a candidate library, a recombinant host cell, an expression construct, an engineered viral vector, or an engineered attenuated virus. In certain embodiments, a reporter gene is under the control of a heterologous promoter responsive to polymerase activity from the first and second polymerase domains when the first and second interaction components interact. In some embodiments, the first and second polymerase domains are truncated portions of a polymerase. It is specifically contemplated that any protein or polypeptide function that are used in embodiments, may be used a nucleic acid encoding that protein or polypeptide function. Also, any and all polypeptides, proteins, nucleic acid molecules may be contained within a cell or other living organism, such as a virus (for instance, a phage).

In some embodiments, there is a kit or system comprising: a) a first polymerase domain attached to a first interaction component; b) a second polymerase domain attached to a second interaction component; c) a nucleic acid construct comprising a reporter gene under the control of a heterologous promoter responsive to polymerase activity from the first and second polymerase domains when the first and second interaction components interact, wherein the first and second polymerase domains are truncated portions of a polymerase. A kit may include one or more components that are separate or together in a suitable container means, such as a sterile, non-reactive container. In some embodiments, cells or viruses are provided that contain one or more nucleic acid constructs that contain a promoter or reporter gene or selection gene or that encode one or more parts of an engineered polymerase system. The term promoter is used according to its ordinary meaning to those in the field of molecular biology; it generally refers to a site on a nucleic acid in which a polymerase can bind to initiate transcription. In specific embodiments, the promoter is recognized by a T7 RNA polymerase.

In other embodiments, there is a kit for screening for modifications to the interaction of a first and second target by a plurality of candidate molecules, comprising a first polymerase domain attached to the first target; a second polymerase domain attached to the second target and a nucleic acid construct comprising a reporter gene under the control of a heterologous promoter responsive to polymerase activity from the first and second polymerase domains when the first and second targets interact, wherein the first and second polymerase domains are truncated portions of a polymerase.

Methods are provided in some embodiments. Methods include, but are not limited to, optimizing interaction of at least first and second interaction components, optimizing interaction of a least first and second interaction components employing a directed evolution process, for identifying a nucleic acid variant, for identifying a polypeptide or peptide variant, for screening for modifications to the interaction of a first and second target by a candidate molecule, for identifying a polypeptide, peptide, or a nucleic acid with altered binding properties, for identifying a molecule that alters binding between two or more interaction components, or for producing a polypeptide, peptide, or a nucleic acid with altered binding properties. Methods further include producing and/or expressing the variant. Methods may be performed in vitro though many embodiments involve performing steps in vivo. In certain embodiments, cells have been transfected with one or more components discussed herein, and they, or their progeny, are used in kits and/or methods.

Embodiments concerns methods of creating and preparing compounds that are modified and that possesses an advantage over a non-modified version of the compound. Methods also concern identifying compounds that modify an interaction among two or more molecules.

In methods described herein, 1, 2, 3, 4, 5 or more of the following steps may be included: incubating components under transcription conditions to create a transcription mixture, incubating or providing a first polymerase domain attached to a first interaction component; incubating or providing a second polymerase domain attached to a second interaction component; incubating or providing a nucleic acid construct comprising a reporter gene under the control of a heterologous promoter responsive to polymerase activity from the first and second polymerase domains when the first and second interaction components interact; assaying for or measuring or detecting expression of the reporter gene; infecting bacteria with phage having a least one essential gene replaced with a nucleic acid sequence encoding a first or second RNA polymerase domain attached to a first or second interaction component, wherein the bacteria expresses another polymerase domain attached to a different interaction component and comprises a nucleic acid construct encoding the replaced essential phage gene under the control of a promoter responsive to RNA polymerase activity from the combined RNA polymerase domains (first and second RNA polymerase domains) when the two different (first and second) interaction components interact; culturing bacteria to allow multiple rounds of replication; culturing bacteria under selective conditions to identify bacteria or phage expressing one or more selective genes; assaying bacteria or phage for expression of one or more exogenous genes; culturing infected bacteria to allow multiple rounds of replication; identifying candidate variant interaction components from any phage clones from cultured bacteria; sequencing any candidate variant interaction components; infecting bacteria with phage having a least one essential gene replaced with a nucleic acid sequence encoding a first T7 RNA polymerase domain attached to a first interaction component, wherein the bacteria expresses a second T7 RNA polymerase domain attached to a second interaction component and comprises a nucleic acid construct encoding the replaced phage essential gene under the control of a promoter responsive to RNA polymerase activity from the first and second T7 RNA polymerase domains when the first and second interaction components interact, wherein the first T7 RNA interaction domain comprises one or more of the following substitutions: L32S, E35G, E63K, K98R, Q107K, T122S or A144T; attaching a first polymerase domain to the first target and attaching a second polymerase domain to the second target, wherein the first and second polymerase domains are truncated portions of a polymerase; incubating the candidate molecule with (i) the first polymerase domain attached to the first target; (ii) the second polymerase domain attached to the second target; (iii) a nucleic acid construct comprising a reporter gene under the control of a heterologous promoter responsive to polymerase activity from the first and second polymerase domains when the first and second targets interact, and analyzing expression of the reporter gene relative to a control; characterizing any identified variant; sequencing any identified variant; culturing cells expressing an identified variant; expressing an identified variant to produce a variant protein, polypeptide or peptide; synthetically producing an identified variant protein, polypeptide, peptide or nucleic acid.

In some embodiments, there are methods for optimizing interaction of at least first and second interaction components comprising: a) incubating the following under transcription conditions to create a transcription mixture: i) a first polymerase domain attached to a first interaction component; ii) a second polymerase domain attached to a second interaction component; iii) a nucleic acid construct comprising a reporter gene under the control of a heterologous promoter responsive to polymerase activity from the first and second polymerase domains when the first and second interaction components interact, wherein the first and second polymerase domains are truncated portions of a polymerase; b) assaying for expression of the reporter gene.

Additional methods include methods for optimizing interaction of a least first and second interaction components employing a directed evolution process, the method comprising a) incubating the following under transcription conditions to create a transcription mixture: i) a first RNA polymerase domain attached to a first interaction component; ii) a second RNA polymerase domain attached to a second interaction component; wherein the first and second polymerase domains are truncated portions of a polymerase; b) infecting bacteria with phage having a least one essential gene replaced with a nucleic acid sequence encoding the first RNA polymerase domain attached to the first interaction component, wherein the bacteria expresses the second RNA polymerase domain attached to the second interaction component and comprises a nucleic acid construct encoding the replaced essential phage gene under the control of a promoter responsive to RNA polymerase activity from the first and second RNA polymerase domains when the first and second interaction components interact; c) culturing the bacteria to allow multiple rounds of replication; and d) identifying the sequence of candidate variant first interaction components from any phage clones from the cultured bacteria.

In further embodiments, there are methods for identifying a nucleic acid variant comprising: a) infecting bacteria with phage having a least one essential gene replaced with a nucleic acid sequence encoding a first RNA polymerase domain attached to a first interaction component, wherein the bacteria expresses a second RNA polymerase domain attached to a second interaction component and comprises a nucleic acid construct encoding the replaced phage essential gene under the control of a promoter responsive to RNA polymerase activity from the first and second RNA polymerase domains when the first and second interaction components interact; b) culturing the bacteria to allow multiple rounds of replication; and c) identifying the nucleic acid variant of the first interaction domain in any phage clone from the cultured bacteria.

Methods are also provided for identifying a nucleic acid variant comprising: a) infecting bacteria with phage having a least one essential gene replaced with a nucleic acid sequence encoding a first T7 RNA polymerase domain attached to a first interaction component, wherein the bacteria expresses a second T7 RNA polymerase domain attached to a second interaction component and comprises a nucleic acid construct encoding the replaced phage essential gene under the control of a promoter responsive to RNA polymerase activity from the first and second T7 RNA polymerase domains when the first and second interaction components interact, wherein the first T7 RNA interaction domain comprises one or more of the following substitutions: L32S, E35G, E63K, K98R, Q107K, T122S or A144T; b) culturing the bacteria to allow multiple rounds of replication; and c) identifying the nucleic acid variant of the first interaction domain in any phage clone from the cultured bacteria.

In further embodiments, there are methods for screening for modifications to the interaction of a first and second target by a candidate molecule, comprising: (a) attaching a first polymerase domain to the first target and attaching a second polymerase domain to the second target, wherein the first and second polymerase domains are truncated portions of a polymerase; (b) incubating the candidate molecule with (i) the first polymerase domain attached to the first target; (ii) the second polymerase domain attached to the second target; (iii) a nucleic acid construct comprising a reporter gene under the control of a heterologous promoter responsive to polymerase activity from the first and second polymerase domains when the first and second targets interact, and (c) analyzing expression of the reporter gene relative to a control. In some embodiments, step a) is omitted.

The nucleic acid construct with the reporter gene is an example of a nucleic acid readout construct responsive to polymerase activity that results from the proximity between the first and second polymerase domains when the first and second targets interact. In other embodiments, a method may assay for the interaction between targets or between interaction components based on the first and second polymerase domains coming together to provide polymerase activity. In various embodiments, a nucleic acid readout construct indicates this qualitatively and/or quantitatively, directly or indirectly. The reporter gene provides an indication of gene expression, which occurs as a result of different domains of an RNA polymerase coming together to provide RNA polymerase activity. In some embodiments, gene expression of the reporter gene results in expression of an RNA transcript that is expressed as a protein, which is measured or evaluated. The protein may be evaluated quantitatively or qualitatively; in some cases, this is done directly, while in others, it is done indirectly by measuring or evaluating something else that is affected by the protein. In some embodiments, this is achieved by measuring one or more activities of the protein. The activity may be colorimetric or fluorescent and/or enzymatic. In some embodiments, the protein does one or more of the following: binds another compound ofor chemical, such as all or part of another protein, nucleic acid, small molecule, tissue, organelle, cell, or chemical compound.

Embodiments cover situations in which the polymerase activity is dependent on the affinity of the first and second interaction components for each other. It is specifically contemplated that any embodiment concerning one or more polymerase domains may involve a engineered polymerase system. In some cases, the different (for example, first and second) polymerase domains are separate polypeptide chains. In certain embodiments, each of the first and second polymerase domains are linked to one of the first and second interaction molecules as fusion proteins.

In some embodiments, there is at least one expression plasmid or vector. It is specifically contemplated that the expression plasmid or vector is extrachromosomal in some embodiments. In certain embodiments, the expression plasmid or vector comprises a phage gene. In some instances, the phage gene is an essential phage gene, meaning the gene is required to generate an infectious phage.

Additional embodiments also concern a reporter gene that is encoded by at least one plasmid or vector. In other embodiments, there may be additional plasmids or vectors. One or more polymerase domains (possibly attached to one or more interaction components or targets) may be encoded by the same or separate expression plasmids. One or more reporter genes, bacterial genes, phage genes, engineered polymerase system components, candidate compounds polymerase domains, interactions components, targets, or selective genes may be encoded on an expression vector, construct or plasmid. They may be encoded on the same or different expression vectors, constructs or plasmids.

In some embodiments, the first and second polymerase domains are from an RNA polymerase. In some instances, the RNA polymerase is a T7 RNA polymerase. In certain embodiments, the T7 RNA polymerase has the sequence provided herein. In further embodiments a first polymerase domain comprises amino acids 1-179 of T7 RNA polymerase and a second polymerase domain comprises amino acids 180-883 of T7 RNA polymerase. In other embodiments, a first polymerase domain comprises a T7 RNA polymerase N-terminal domain and a second polymerase domain comprises a T7 RNA polymerase C-terminal domain. In additional embodiments, a polymerase domain comprises an amino acid substitution relative to a wild-type sequence. In specific embodiments, a T7 RNA polymerase N-terminal domain, the T7 RNA polymerase C-terminal domain or both comprise one or more amino acid substitutions. In some embodiments, the one or more amino acid substitutions correspond to positions 32, 35, 63, 98, 107, 122, or 144 of the T7 RNA polymerase disclosed herein. A person of ordinary skill in the art can recognize that the position may not be exactly the same among different T7 polymerase, but that person would know which position corresponds to the recited position because of the homology/ identify among different T7 RNA polymerase family members such that corresponding amino acids can be lined up to one another. In some cases, 1, 2, 3, 4, 5, 6, or 7 amino acid substitutions (or any range derivable therein) that are L32S, E35G, E63K, K98R, Q107K, T122S or A144T corresponding to SEQ ID NO:4 are included in a T7 RNA polymerase domain. In some cases, the first polymerase domain comprises at least 3 amino acid substitutions that are L32S, E35G, E63K, K98R, Q107K, T122S or A144T. In other embodiments, the first polymerase domain comprises amino acid substitutions that are L32S, E35G, E63K, K98R, Q107K, T122S and A144T. Moreover, in some embodiments, the first polymerase domain comprises amino acid substitutions that are L32S, E35G, K98R, Q107K, T122S and A144T. In some cases, 1, 2, 3, 4, 5, 6, or 7 amino acid substitutions (or any range derivable therein) that are L32S, E35G, E63K, K98R, Q107K, T122S or A144T corresponding to SEQ. ID. NO:4 are included in a T7 RNA polymerase domain that is otherwise 80, 81, 82, 83, 84, 85, 86, 87, 88, 89, 90, 91, 92, 93, 94, 95, 96, 97, 98, 99, or 100% (or any range derivable therein) identical to SEQ ID NO:4.

In some aspects, the reporter gene is under the control of a T7 promoter. The reporter gene may be enzymatic, luminescent, color-producing, electrical, radioactive, or fluorescent. In certain embodiments, a reporter gene encodes a luciferase protein. In other embodiments, a reporter gene encodes a RNA nanostructure, an mRNA encoding a reporter protein or an RNAi.

Additional embodiments include a negative control nucleic acid encoding a dominant negative polypeptide that cannot interact with the first or second interaction component. In some embodiments, the dominant negative polypeptide is attached to an alternate first or alternate second polymerase domain and the system further comprises a second heterologous promoter responsive to polymerase activity from either (a) the first and alternate second polymerase domains or (b) the alternate first and the second polymerase domains, when the first and alternate second polymerase domains or the alternate first and the second polymerase domains interact. In some embodiments, the alternate first or alternate second polymerase domains comprise one or more mutations relative to the first or second polymerase domains, respectively. In some cases, the alternate first or alternate second polymerase domains are 80%, 85%, 90%, 95%, 97%, 98% or 99% identical to the first or second polymerase domains, respectively (and any range derivable therein).

In some embodiments, there is a second reporter gene. In further embodiments, a second reporter gene is under the control of the second heterologous promoter.

In some aspects, a first or second reporter gene enables a positive selection event and the second reporter gene enables a negative selection event.

Other embodiments include where the affinity of the first and second interaction components is modulated by light.

In some cases, the first interaction component is a peptide, polypeptide, a nucleic acid, or a small molecule. Additionally, it is contemplated that the second interaction component is a peptide, polypeptide, a nucleic acid, or a chemical compound. In specific embodiments, the first and second interaction components are peptides or polypeptides. In some cases, the first and second interaction components dimerize or are brought into proximity by interaction with a third interaction component, which may or may not be a small molecule.

Embodiments may include a recombinant host cell. In some embodiments, the host cell is a bacterial cell or a mammalian cell. In some cases, the mammalian cell is a heterologous cell line cell.

In some embodiments, methods involve incubating one or more candidate agents with the transcription mixture to evaluate whether one or more candidate agents modifies the interaction between the interaction components. In some embodiments, polymerase activity is dependent on the affinity of the first and second interaction components for each other. In some instances, the first and second polymerase domains are separate polypeptide chains. In particular cases, each of the first and second polymerase domains are linked to one of the first and second interaction molecules as fusion proteins. A modification in the interaction is evidenced by a change in transcription of about, at least about or at most about 5, 10, 15, 20, 25, 30, 35, 40, 45, 50, 60, 70, 80, 90, 100, 110, 120, 130, 140, or 150% and/or by about, at least about, or at most about 2×, 3×, 4×, 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000× (or any range derivable therein) relative to a control. The change may be an increase or a decrease in transcription.

In specific embodiments, methods involve evaluating for a negative modification on the interaction. This means evaluating one or more candidate agents for an ability to inhibit, interfere with, reduce, or otherwise negatively impact the interaction between interaction components. In some embodiments, transcription is reduced by about, at least about or at most about 5, 10, 15, 20, 25, 30, 35, 40, 45, 50, 60, 70, 80, 90, 100, 110, 120, 130, 140, or 150% and/or by about, at least about, or at most about 2×, 3×, 4×, 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000× (or any range derivable therein) relative to a control. The control may be a positive control and/or there may be a negative control. In certain embodiments, there is a method of screening for a candidate inhibitor comprising (a) incubating one or more candidate agents with (i) a first polymerase domain attached to the first interaction component; (ii) a second polymerase domain attached to a second interaction component; (iii) a nucleic acid readout construct responsive to polymerase activity from the first and second polymerase domains when the first and second components interact, and (b) analyzing the readout from the nucleic acid readout construct relative to a control. In some embodiments, the nucleic acid readout construct comprises a reporter gene under the control of a heterologous promoter responsive to polymerase activity from the first and second polymerase domains when the first and second targets interact. A candidate inhibitor is identified if the readout indicates the candidate agent is reducing or interfering with the first and second polymerase domains from coming together to generate polymerase activity or function.

Methods may also further include providing at least one expression plasmid. In some embodiments, an expression plasmid comprises a phage gene. In some embodiments, a reporter gene is encoded by at least one plasmid, which may be referred to as a reporter plasmid.

In some embodiments, the first polymerase domain and the second polymerase domain are encoded by separate expression plasmids. In specific examples, the first and second polymerase domains are from an RNA polymerase. More specifically, in some cases, the first and second polymerase domains are from a T7 RNA polymerase.

In specific embodiments, the interaction domain is a polypeptide or nucleic acid or small molecule. It is specifically contemplated that one or more of these may be excluded in a particular embodiment. The term "small molecule" refers to a low molecular weight (<900 daltons) organic compound that may help regulate a biological process, with a size on the order of $10^{-9}$ m.

In specific embodiments, the reporter gene encodes a guide RNA that is used with a CRISPR system or other genome editing technology. This means the guide RNA contains the relevant sequence recognition signal for the relevant enzyme. In some embodiments, evaluating or measuring gene expression involves evaluating or measuring a result of expressing a guide RNA in the context of a guide-RNA-directed gene editing process. The guide RNA may be targeted to a gene that, when edited and expressed, can be evaluated or measured. In specific embodiments, the genome editing technology is Cas9 or Cpf1. The edited gene (which can be corrected, mutated, or changed) may be expressed and its expression may be measured as an RNA transcript, as an expressed protein, or based on an activity, function, or localization of the protein expressed from the edited gene. Some embodiments include one or more of the following: a nuclease, a reporter gene encoding a guide RNA, a target gene for the guide RNA. Methods may involve incubating one or more of these gene editing components. In some embodiments, there is a method of using a gene editing technology to evaluate an interaction between two components comprising: a) incubating in a cell comprising a target gene (i) a first polymerase domain attached to the first interaction component; (ii) a second polymerase domain attached to a second interaction component; (iii) a reporter gene under the control of a promoter that is functional based on polymerase activity from the first and second polymerase domains when the first and second components interact, wherein the reporter gene encodes a guide RNA to edit a target gene; b) determining whether the target gene has been edited based on the guide RNA. This may involve assaying for expression or activity of the gene product of the edited (or unedited) reporter gene. A negative and/or positive control may also be assayed and/or may be used as a comparison point.

Methods involve employing a directed evolution process. In some embodiments, variants are introduced into nucleic acids or proteins. The variants may be deletions, insertions, or substitutions, or a combination thereof. Modifications may improve interactions but in some cases, modifications may reduce interactions. The latter may be desirable for a number of reasons, including reducing immunogenicity. In certain embodiments, an antibody is the focus of a directed evolution process. In some embodiments, biomolecular interactions can be optimized using rapid continuous evolution. The fusion on the optimized and evolved N-terminal RNAP half can be changed to a target protein that is to be optimized and cloned into an M13 evolution phage. Accessory plasmids (APs) can be engineered that express a target antigen fused to the C-terminal RNAP half. In this way, phage will evolve interactions between the N-terminal tagged protein and the C-terminal tagged bait. Negative selection can also be implemented by tethering an off-target antigen to an orthogonal C-terminal RNAP tag and driving counterselection pressure. The assays described herein can be employed to evaluate the evolved proteins based on their interactions. The evolution process may be repeated multiple times. The evolved antibody may then be expressed and/or produced. The process may involve all or part of an antibody, such as a variable region or a portion of a variable region, or it may involve an antibody derivative, such as a single chain antibody.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D—Design and biophysical feasibility of activity-responsive RNA polymerases (ARs) based on proximity-dependent split RNAPs. (a) Schematic depiction of AR design. Split T7 RNAP engineered such that it assembles into a functional RNAP when proteins of interest (POIs) fused to each half interact with one another, resulting in transcription of a user-defined sequence of RNA from a supplied DNA substrate. (b) Vectors designed to test split RNAPs in vivo, including a luciferase reporter vector and expression vectors for each of the two halves of the split RNAP. (c) Schematic of the components utilized to test split RNAP assembly, including N-terminal split RNAP, C-terminal split RNAP, and model protein-protein interaction domains including anti-parallel leucine zipper peptide fusions, ZA, ZB and ZBneg (black). ZA and ZB form a tight interaction with one another; ZBneg has three point mutations compared to ZB that dramatically weaken the interaction. (d) Transcriptional output of split RNAPs with fusion proteins assayed in E. coli. using the vectors shown in (c). Cells induced for 2 h with arabinose and then analyzed for luminescence (error bars std. error, n=4). Fusion of the peptides does not interfere with RNAP assembly. Transcription is enhanced if fused peptides interact.

FIGS. 2A-E—Evolution of a proximity-dependent split RNAP for protein-protein interaction detection. (a) Phage-assisted continuous evolution (PACE) system for proximity dependent RNAPs. Phage carry an evolving N-terminal RNAP fused to ZA, which is given a constant choice of assembling with either a C-terminal RNAP variant fused to the ZB binding partner that produces gIII and allows phage replication, or a C-terminal RNAP variant that is fused to the non-interacting ZBneg partner, which poisons phage production by producing a dominant negative form of gIII (gIIIneg). The concentrations of the two competing binding partners are carefully tuned during the course of the evolution. (b) Schematic of the evolution parameters used during the course of PACE. The RBS strengths (Ringquist, et al., 1992) controlling the expression of the C-terminal RNAPs on both the posAP and negAP, the RBSs controlling the output gIII or gIIneg, and the copy number of the posAP, were carefully tuned during the course of the 29 days of evolution. (c) Genotype of the two main N-terminal variants that were converged upon during 29 days of PACE. (d) Mapping the mutations of N-29-1 onto the T7 RNAP crystal structure (PDB 1QLN). (e) Transcriptional reporter assay of the two primary N-terminal split RNAP genotypes fused to ZA interacting with either the C-terminal RNAP fused to ZB (blue) or ZBneg (grey) (error bars std. error, n=4). During PACE, the antiparallel leucine zipper also evolved to a double mutant, and inclusion of the optimized PPI mutations resulted in a robust enhancement in transcription.

FIGS. 3A-D—Small molecule and light-responsive ARs. (a) Schematic of light activated RNAP design using iLID-nano system fused to the evolved split RNAP. (b) Transcription response of the light-activated RNAP system in E. coli. Cells transformed with expression vectors for the two halves of the light-inducible RNAP and a reporter vector, then either kept in the dark or illuminated with blue LED light for 3 h prior to transcriptional analysis (error bars std. error, n=4). (c) Schematic of small molecule responsive RNAP design using FRB and FKBP fused to the evolved split RNAP. (d) Transcription response of the rapamycin-inducible RNAP system in E. coli. Cells transformed with expression vectors for the two halves of the small molecule-inducible RNAP and a reporter vector, then induced with varying concentrations of rapamycin for 3 h prior to transcription analysis (error bars std. error, n=4).

FIGS. 4A-D—ARs can trigger a variety of outputs in mammalian cells. (a) Design of the "rapa-T7" vector for rapamycin induced transgene expression in mammalian systems. (b) Validation of the rapa-T7 vector with a fluorescent RNA aptamer as the output. HEK293T cells transfected with the rapa-T7-F30-2×dBroccoli vector and induced with 0 or 100 nM rapamycin for 30 min in the presence of 20 µM DHFBI-1T then analyzed by fluorescence microscopy. 100 µm scale bar shown. (c) Validation of the rapa-T7 vector with mRNA as the output. HEK293T cells transfected with the rapa-T7-mRNA(GFP) vector induced with 0 or 10 nM rapamycin overnight then analyzed by fluorescence microscopy (100 µm scale bar shown). (d) Validation of the rapa-T7 vector with shRNA as the output. HEK293T cells transfected with a GFP expression vector and a rapa-T7-shRNA (GFP) vector and induced with varying concentrations of rapamycin for 44 h. GFP fluorescence analyzed by flow cytometry (error bars std. error, n=3).

FIGS. 5A-G—Vectors and plasmid maps

FIG. 6—A schematic of the complete evolutionary protocol

FIGS. 7A-C—Results of the sequence analysis during the course of the evolution

DESCRIPTION OF ILLUSTRATIVE EMBODIMENTS

I. Methods and Compositions

Biosensors that transduce target chemical and biochemical inputs into genetic outputs are essential for bioengineering and synthetic biology. The inventors report the development of a proximity-dependent split RNA polymerase (RNAP) as a general platform for biosensor engineering. After discovering that interactions between fused proteins modulate the assembly of a split T7 RNAP, the inventors optimized the split RNAP components for protein-protein interaction detection by phage-assisted continuous evolution (PACE). The inventors then applied the resulting "activity-responsive RNAP" (AR) system to create light and small molecule activated biosensors. The inventors also validated that split RNAP-based biosensors can trigger RNA nanostructure production, protein synthesis, and gene knockdown in mammalian systems, illustrating the versatility of ARs in synthetic biology applications.

II. Nucleic Acids

In certain embodiments, there are recombinant nucleic acids encoding the proteins, polypeptides, or peptides described herein. Polynucleotides contemplated for use in methods and compositions include those encoding polymerases, in particular RNA polymerases. Also contemplated are polynucleotides encoding interaction components that are proteins known to, suspected to or expected to interact or bind to each other.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., a polymerase, RNA polymerase, one or more truncated polymerase domains or interaction components that are polypeptides) that drive gene transcription dependent on polymerase activity from the polymerase domains when the interaction components interact. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which it is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce a polymerase, RNA polymerase, one or more truncated polymerase domains or interaction components that are fused, attached or linked to the one or more truncated RNA polymerase domains.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. Proteinaceous Compositions

The polypeptides, first polymerase domain or second polymerase domains described herein may include 1, 2, 3, 4, 5, 6, 7, 8, 9, 10, 11, 12, 13, 14, 15, or more variant amino acids or be at least 70%, 80%, 85%, 90%, 95%, 98%, 99% or 100% similar or identical within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 1-8.

A polypeptide, first polymerase domain or second polymerase domains segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO: 1-8.

In some embodiments, the first polymerase domain may comprise amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 of SEQ ID NO: 4, 6 or 8.

In other embodiments, the second polymerase domain may comprise amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702 or 703 of SEQ ID NO: 2.

In specific embodiments, a first polymerase domain may be a T7 RNA polymerase domain N-terminal truncation. In other aspects, the T7 RNA polymerase N-terminal truncation may comprise one or more amino acid substitutions at positions 32, 35, 63, 98, 107, 122 or 144 of SEQ ID NO: 4, 6 or 8 or at positions corresponding to positions 32, 35, 63, 98, 107, 122 or 144 of SEQ ID NO: 4, 6 or 8. In some instances, a corresponding position may be determined by alignment, homology or similarity. In certain aspects the substitutions are one or more of a L32S, E35G, E63K, K98R, Q107K, T122S or A144T substitution of SEQ ID NO: 4, 6 or 8 or positions corresponding to SEQ ID NO: 4, 6 or 8. In particular embodiments, there is a domain comprising 1, 2, 3, 4, 5, 6, or 7 (or any range derivable therein) substitutions that are selected from L32S, E35G, E63K, K98R, Q107K, T122S or A144T of SEQ ID NO: 4, 6 or 8 or positions corresponding to SEQ ID NO: 4, 6 or 8 and the domain is otherwise 80, 81, 82, 83, 84, 85, 86, 87, 88, 89, 90, 91, 92, 93, 94, 95, 96, 97, 98, 99, or 100% (or any range derivable therein) identical to SEQ ID NO:4, SEQ ID NO:6, or SEQ ID NO:8.

In some aspects a truncated RNA polymerase domain comprises mutations that affect the recognition site to initiate transcription. In some aspects, the second domain comprises mutations that affect the recognition site to initiate transcription. In certain aspects a mutated T7 RNA polymerase second domain does not initiate transcription from a T7 promoter when in proximity of a T7 RNA polymerase first domain. In other aspects a mutated T7 RNA polymerase second domain initiates transcription from a non-T7 promoter when in proximity of a T7 RNA polymerase first domain (e.g. a CGG promoter).

In certain aspects an RNA polymerase or the truncated domains from an RNA polymerase are from a T7, T3, K11 or SP6 RNA polymerase. In other aspects the RNA polymerase is a RNA polymerase I, RNA polymerase II, RNA polymerase III, RNA polymerase IV or RNA polymerase V.

In particular embodiments, a first polymerase domain may comprise all or any part of the N-terminal portion of an RNA polymerase or an RNA polymerase that is functionally, structurally, or both functionally and structurally related to an RNA polymerase of bacteriophage T7 (i.e., a T7-related RNA polymerase). In some aspects, a first polymerase domain comprises all or any part of a component from an RNA polymerase or a T7-related RNA polymerase. In the present context, the term component refers to any contiguous sequence of amino acids from an RNA polymerase or a T7-related RNA polymerase, in particular contiguous amino acid sequences that define structural, functional or structural and functional components of an RNA polymerase or a T7-related RNA polymerase. Examples of structural and functional components of an RNA polymerase or of a T7-related RNA polymerase are described in Tunitskaya, V. L. & Kochetkov, S. N. Biochemistry (2002) 67: 1124 and in Shis D L & Bennett M R., Proc Natl Acad Sci USA. 2013 Mar. 26; 110(13):5028-33, the contents of which, for both, are hereby incorporated by reference. For example, a contiguous sequence of amino acids from an RNA polymerase or a T7-related RNA polymerase may comprise up to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids from the N-terminal portion of an RNA polymerase or a T7-related RNA polymerase. In the context of the first polymerase domain, a component from an RNA polymerase or a T7-related RNA polymerase may comprise all or part of the H-loop domain from an RNA polymerase or a T7-related RNA polymerase. In other aspects, a component from an RNA polymerase or a T7-related RNA polymerase comprises all or a part of an N-terminal platform protein domain from an RNA polymerase or a T7-related RNA polymerase. In particular aspects, a component from an RNA polymerase or a T7-related RNA polymerase comprises all or part of a domain that transitions the transcription initiation complex or process to a transcription elongation complex or process. In yet other aspects, a first polymerase domain comprises all or part of a subdomain from a T7-related RNA polymerase that transitions the transcription initiation complex or process to a transcription elongation complex or process. In specific aspects, the first polymerase domain of a T7-related RNA polymerase comprising a component as defined above is attached to a first interaction component.

In other aspects, a second polymerase domain may comprise all or any part of the C-terminal portion of an RNA polymerase or from a RNA polymerase that is functionally, structurally or functionally and structurally related to an RNA polymerase of bacteriophage T7 (i.e., a T7-related RNA polymerase). In some aspects, a second polymerase domain comprises all or any part of a component from an RNA polymerase or a T7-related RNA polymerase. In the present context, the term component refers to any contiguous sequence of amino acids from an RNA polymerase or a T7-related RNA polymerase, in particular contiguous amino acid sequences that define structural, functional or structural and functional components of an RNA polymerase or a T7-related RNA polymerase. Examples of structural and functional components of an RNA polymerase or of a T7-related RNA polymerase are described in Tunitskaya, V. L. & Kochetkov, S. N. Biochemistry (2002) 67: 1124 and in Shis D L & Bennett M R., Proc Natl Acad Sci USA. 2013 Mar. 26; 110(13):5028-33, the contents of which, for both, are hereby incorporated by reference. For example, a contiguous sequence of amino acids from an RNA polymerase or a T7-related RNA polymerase may comprise up to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 750, 800, 850, 900, 950 or 1000 or more contiguous amino acids from the C-terminal portion of an RNA polymerase or a T7-related RNA polymerase. In the context of the second polymerase domain, a component from an RNA polymerase or a T7-related RNA polymerase may comprise all or part of the specificity domain of an RNA polymerase or a T7-related RNA polymerase. In particular embodiments, a component from an RNA polymerase or a T7-related RNA polymerase may comprise all, or a part of the polymerization domain of an RNA polymerase or a T7-related RNA polymerase. In other embodiments, a component from an RNA polymerase or a T7-related RNA polymerase may comprise all or a part of at least one of the palm, thumb or finger subdomains of a RNA polymerase or a T7-related RNA polymerase. In still other embodiments, a component from an RNA polymerase or a T7-related RNA polymerase may comprise all, or a part of at least one of the A, B or C motifs of an RNA polymerase or a T7-related RNA polymerase. In certain embodiments, a component from an RNA polymerase or a T7-related RNA polymerase comprised in a second polymerase domain binds a target promoter sequence and initiates initial or abortive transcription of a template driven by or downstream of the promoter. In specific aspects, the second polymerase domain of a T7-related RNA polymerase comprising a component as defined above is attached to a second interaction component. In further aspects, binding affinity of the first and second interaction components for each other, where each is attached to the first and second polymerase domains of a T7-related RNA polymerase, respectively, transitions the transcription initiation complex or activity of the second polymerase domain to a transcription elongation complex or process.

In particular embodiments, an polymerase, an RNA polymerase, a T7, T3, K11 or SP6 RNA polymerase, or a T7-related RNA polymerase is separated into a first and second polymerase domains by selecting an amino acid boundary or junction that separates or decouples the specificity and polymerization domains from a domain that transitions a transcription initiation complex or activity to a transcription elongation complex or activity.

In some embodiments, a polymerase, RNA polymerase, one or more truncated RNA polymerase domains, or interaction components may be isolated. The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity, ability of a polymerase to drive transcription or ability of truncated polymerase domains to drive transcription from heterologous promoters when the truncated domains are brought into proximity. Structures such as, for example, a polymerase, RNA polymerase, one or more truncated RNA polymerase domains, or interaction components may have amino acid substituted to maintain such function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In other embodiments, alteration of the function of a polymerase, RNA polymerase, truncated RNA polymerase domains or two or more interaction components is intended by introducing one or more substitutions. For example, certain amino acids may be substituted for other amino acids in a protein structure with the intent to modify the interactive binding capacity of interaction components or of the ability of a polymerase to drive transcription or the ability of truncated polymerase domains to drive transcription from heterologous promoters when the truncated domains are brought into proximity. Structures such as, for example, a polymerase, RNA polymerase, one or more truncated RNA polymerase domains, or interaction components may have amino acid substituted to alter such function. Since it is the interactive capacity and nature of a protein that defines that protein's biological functional activity, certain amino acid substitutions can be made in a protein sequence, and in its underlying DNA coding sequence, and nevertheless produce a protein with different properties. It is thus contemplated by the inventors that various changes may be made in the DNA sequences of genes with appreciable alteration of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

Polypeptides and Polypeptide Production

Embodiments involve a polymerase, RNA polymerase, one or more truncated RNA polymerase domains, or interaction components for use in various aspects described herein. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In certain aspects a polymerase, RNA polymerase, one or more truncated RNA polymerase domains which has at least 85% identity, at least 90% identity, at least 95% identity, or at least 97-99% identity, including all values and ranges there between, to a sequence selected over the length of the fragment sequence. In yet other aspects, an interaction component comprises substantially some or all of the antigenic portion a protein which has at least 85% identity, at least 90% identity, at least 95% identity, or at least 97-99% identity, including all values and ranges there between, to a sequence selected over the length of the fragment sequence (e.g. for the sequences given by at least one of SEQ ID NO: 1-8).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods

Cloning. All plasmids were constructed by Gibson Assembly (Gibson, 2009) from PCR products generated using Q5 Hot Start DNA Polymerase (NEB) or Phusion Polymerase. Phage were cloned by Gibson Assembly of the split N-terminal RNAP-ZA fusion into a previously optimized SP phage backbone (Dickinson, et al., 2014) and transformation into 1059 cells (Carlson, et al., 2014), which supply gIII in an activity-independent manner. After overnight growth in media, the supernatant was isolated by centrifugation and plaque assays were performed on 1059 cells. Single plaques were selected for overnight growth and sequencing to identify clonal phage samples with the correct insert. All plasmids and phage were sequenced at the University of Chicago Comprehensive Cancer Center DNA Sequencing and Genotyping Facility. Vectors and plasmid maps are depicted in FIG. 5.

Sequence of split RNAP fusions. Shown below are the structures and sequences of the leucine zipper peptide fusions, iLID-nano light-induced dimerization fusions, and rapamycin-induced dimerization constructs used in this study. Linkers are italicized and the fusion proteins are underlined. The three point mutations between ZB and ZBneg are underlined and were obtained from previous studies (Magliery, et al., 2005).

C-term RNAP (WT)

(SEQ ID NO: 1)
aaagcatttatgcaagttgtcgaggctgacatgctctctaagggtctact cggtggcgaggcgtggtcttcgtggcataaggaagactctattcatgtag gagtacgctgcatcgagatgctcattgagtcaaccggaatggttagctta caccgccaaaatgctggcgtagtaggtcaagactctgagactatcgaact cgcacctgaatacgctgaggctatcgcaacccgtgcaggtgcgctggctg gcatctctccgatgttccaaccttgcgtagttcctcctaagccgtggact ggcattactggtggtggctattgggctaacggtcgtcgtcctctggcgct ggtgcgtactcacagtaagaaagcactgatgcgctacgaagacgtttaca tgcctgaggtgtacaaagcgattaacattgcgcaaaacaccgcatggaaa atcaacaagaaagtcctagcggtcgccaacgtaatcaccaagtggaagca ttgtccggtcgaggacatccctgcgattgagcgtgaagaactcccgatga aaccggaagacatcgacatgaatcctgaggctctcaccgcgtggaaacgt gctgccgctgctgtgtaccgcaaggacaaggctcgcaagtctcgccgtat cagccttgagttcatgcttgagcaagccaataagtttgctaaccataagg ccatctggttcccttacaacatggactggcgcggtcgtgtttacgctgtg tcaatgttcaacccgcaaggtaacgatatgaccaaaggactgcttacgct ggcgaaaggtaaaccaatcggtaaggaaggttactactggctgaaaatcc acggtgcaaactgtgcgggtgtcgataaggttccgttccctgagcgcatc aagttcattgaggaaaaccacgagaacatcatggcttgcgctaagtctcc actggagaacacttggtgggctgagcaagattctccgttctgcttccttg cgttctgctttgagtacgctggggtacagcaccacggcctgagctataac tgctcccttccgctggcgtttgacgggtcttgctctggcatccagcactt ctccgcgatgctccgagatgaggtaggtggtcgcgcggttaacttgcttc ctagtgaaaccgttcaggacatctacgggattgttgctaagaaagtcaac gagattctacaagcagacgcaatcaatgggaccgataacgaagtagttac cgtgaccgatgagaacactggtgaaatctctgagaaagtcaagctgggca ctaaggcactggctggtcaatggctggcttacggtgttactcgcagtgtg actaagcgttcagtcatgacgctggcttacgggtccaaagagttcggctt ccgtcaacaagtgctggaagataccattcagccagctattgattccggca agggtctgatgttcactcagccgaatcaggctgctggatacatggctaag ctgatttgggaatctgtgagcgtgacggtggtagctgcggttgaagcaat

```
gaactggcttaagtctgctgctaagctgctggctgctgaggtcaaagata agaagactggagagattcttcgcaagcgttgcgctgtgcattgggtaact cctgatggtttccctgtgtggcaggaatacaagaagcctattcagacgcg cttgaacctgatgttcctcggtcagttccgcttacagcctaccattaaca ccaacaaagatagcgagattgatgcacacaaacaggagtctggtatcgct cctaactttgtacacagccaagacggtagccaccttcgtaagactgtagt gtgggcacacgagaagtacggaatcgaatcttttgcactgattcacgact ccttcggtaccattccggctgacgctgcgaacctgttcaaagcagtgcgc gaaactatggttgacacatatgagtcttgtgatgtactggctgatttcta cgaccagttcgctgaccagttgcacgagtctcaattggacaaaatgccag cacttccggctaaaggtaacttgaacctccgtgacatcttagagtcggac ttcgcgttcgcgtaa
```

(SEQ ID NO: 2)
```
KAFMQVVEADMLSKGLLGGEAWSSWHKEDSIHVGVRCIEMLIESTGMVSL
HRQNAGVVGQDSETIELAPEYAEAIATRAGALAGISPMFQPCVVPPKPWT
GITGGGYWANGRRPLALVRTHSKKALMRYEDVYMPEVYKAINIAQNTAWK
INKKVLAVANVITKWKHCPVEDIPAIEREELPMKPEDIDMNPEALTAWKR
AAAAVYRKDKARKSRRISLEFMLEQANKFANHKAIWFPYNMDWRGRVYAV
SMFNPQGNDMTKGLLTLAKGKPIGKEGYYWLKIHGANCAGVDKVPFPERI
KFIEENHENIMACAKSPLENTWWAEQDSPFCFLAFCFEYAGVQHHGLSYN
CSLPLAFDGSCSGIQHFSAMLRDEVGGRAVNLLPSETVQDIYGIVAKKVN
EILQADAINGTDNEVVTVTDENTGEISEKVKLGTKALAGQWLAYGVTRSV
TKRSVMTLAYGSKEFGFRQQVLEDTIQPAIDSGKGLMFTQPNQAAGYMAK
LIWESVSVTVVAAVEAMNWLKSAAKLLAAEVKDKKTGEILRKRCAVHWVT
PDGFPVWQEYKKPIQTRLNLMFLGQFRLQPTINTNKDSEIDAHKQESGIA
PNFVHSQDGSHLRKTVVWAHEKYGIESFALIHDSFGTIPADAANLFKAVR
ETMVDTYESCDVLADFYDQFADQLHESQLDKMPALPAKGNLNLRDILESD
FAFA
```

N-term RNAP (WT)

(SEQ ID NO: 3)
```
Atgaacacgattaacatcgctaagaacgacttctctgacatcgaactggc
tgctatcccgttcaacactctggctgaccattacggtgagcgtttagctc
gcgaacagttggccatgagcatgagtcttacgagatgggtgaagcacgct
tccgcaagatgtttgagcgtcaacttaaagctggtgaggttgcggataac
gctgccgccaagcctctcatcactaccctactccctaagatgattgcacg
catcaacgactggtttgaggaagtgaaagctaagcgcggcaagcgcccga
cagccttccagttcctgcaagaaatcaagccggaagccgtagcgtacatc
accattaagaccactctggcttgcctaaccagtgctgacaatacaaccgt
tcaggctgtagcaagcgcaatcggtcgggccattgaggacgaggctcgct
tcggtcgtatccgtgaccttgaagctaagcacttcaagaaaaacgttgag
gaacaactcaacaagcgcgtagggcacgtctacaag
```

(SEQ ID NO: 4)
```
MNTINIAKNDFSDIELAAIPFNTLADHYGERLAREQLALEHESYEMGEAR
FRKMFERQLKAGEVADNAAAKPLITTLLPKMIARINDWFEEVKAKRGKRP
TAFQFLQEIKPEAVAYITIKTTLACLTSADNTTVQAVASAIGRAIEDEAR
FGRIRDLEAKHFKKNVEEQLNKRVGHVYK
```

N-term RNAP(N-29-1)

(SEQ ID NO: 5)
```
atgaacacgattaacatcgctaagaacgacttctctgacatcgaactggc
tgctatcccgttcaacactctggctgaccattacggtgagcgtTCAgctc
gcGGAcagttggcccttgagcatgagtcttacgagatgggtgaagcacgc
ttccgcaagatgtttgagcgtcaacttaaagctggtgaggttgcggataa
cgctgccgccaagcctctcatcactaccctactccctaagatgattGCCc
gcatcaacgactggtttgaggaagtgaaagctaagcgcggcAGGcgcccg
acagccttccagttcCTAAAgaaatcaagccggaagccgtagcgtacat
caccattaagaccTCTctggcttgcctaaccagtgctgacaatacaaccg
ttcaggctgtagcaagcgcaatcggtcggACCattgaggacgaggctcgc
ttcggtcgtatccgtgaccttgaagctaagcacttcaagaaaaacgttga
ggaacaactcaacaagcgcgtagggcacgtctacaag
```

(SEQ ID NO: 6)
```
MNTINIAKNDFSDIELAAIPFNTLADHYGERSARGQLALEHESYEMGEAR
FRKMFERQLKAGEVADNAAAKPLITTLLPKMIARINDWFEEVKAKRGRRP
TAFQFLKEIKPEAVAYITIKTSLACLTSADNTTVQAVASAIGRTIEDEAR
FGRIRDLEAKHFKKNVEEQLNKRVGHVYK
```

N-term RNAP(N-29-8)

(SEQ ID NO: 7)
```
atgaacacgattaacatcgctaagaacgacttctctgacatcgaactggc
tgctatcccgttcaacactctggctgaccattacggtgagcgtTCAgctc
gcGGAcagttggcccttgagcatgagtcttacgagatgggtgaagcacgc
ttccgcaagatgtttgagcgtcaacttaaagctggtAAGgttgcggataa
cgctgccgccaagcctctcatcactaccctactccctaagatgattGCCc
gcatcaacgactggtttgaggaagtgaaagctaagcgcggcAGGcgcccg
acagccttccagttcCTAAAgaaatcaagccggaagccgtagcgtacat
caccattaagaccTCTctggcttgcctaaccagtgctgacaatacaaccg
ttcaggctgtagcaagcgcaatcggtcggACCattgaggacgaggctcgc
ttcggtcgtatccgtgaccttgaagctaagcacttcaagaaaaacgttga
ggaacaactcaacaagcgcgtagggcacgtctacaag
```

(SEQ ID NO: 8)
```
MNTINIAKNDFSDIELAAIPFNTLADHYGERSARGQLALEHESYEMGEAR
FRKMFERQLKAGKVADNAAAKPLITTLLPKMIARINDWFEEVKAKRGRRP
TAFQFLKEIKPEAVAYITIKTSLACLTSADNTTVQAVASAIGRTIEDEAR
FGRIRDLEAKHFKKNVEEQLNKRVGHVYK
```

-continued

N-ZA:
(SEQ ID NO: 9)
RNAP(1-179)-*GGSGSGSS*-ALKKELQANKKELAQLKWELQALKKELAQ

C-ZB:
(SEQ ID NO: 10)
MASEQLEKKLQALEKKLAQLEWKNQALEKKLAQ-*TSGGSG*-RNAP(180+)

C-ZBneg:
(SEQ ID NO: 11)
MASEQLEKELQALEKELAQLKWKNQALEKKLAQ-*TSGGSG*-RNAP(180+)

N-ZA-(L13I,L20I):
(SEQ ID NO: 12)
N-28-1(1-179)-*GGSGSGSS*-ALKKELQANKKEIAQLKWEIQALKKELAQ

N-term-iLID:
(SEQ ID NO: 13)
N-28-1(1-179)-*GGSGSGSS*-iLID

SspB-C-term:
(SEQ ID NO: 14)
SspB_nano-*TSGGSG*-RNAP(180+)

N-term-FRB:
(SEQ ID NO: 15)
N-28-1(1-179)-*GGSGSGSS*-FRB

FKBP-C-term:
(SEQ ID NO: 16)
FKBP-*TSGGSG*-RNAP(180+)

In vivo transcription assays of split RNAPs. N- and C-terminal halves of the RNAP were cloned into expression vectors, with the N-terminal RNAP under a constitutive promoter and the C-terminal RNAP under the arabinose-inducible promoter (Supplementary FIG. 1). S1030 cells (Carlson, et al., 2014) were transformed by electroporation with three plasmids: (i) an N-terminal RNAP expression plasmid, (ii) a C-terminal expression plasmid, and (iii) a reporter plasmid that encodes luciferase under control of the T7 promoter. The transformed cells were then plated onto agar plates (15 g/L in LB) with 50 µg/mL carbenicillin, 50 µg/mL spectinomycin, 33 µg/mL chloramphenicol, and 10 mM glucose. Single colonies were then grown to saturation overnight at 37° C., and then each well of a 96-well deep well plate containing 0.54 mL of LB with antibiotics and 10 mM arabinose was innoculated with 60 µL of the overnight culture. After growth with shaking at 37° C. for 2 h, 150 µL of each culture was transferred to a 96-well black wall, clear bottom plate (Costar), and luminescence and OD600 was measured on a Synergy H4 Hybrid Reader (BioTek). The data were analyzed by dividing the luminescence values by the background-corrected OD600 value, then subtracting out the background from the reporter vector alone. All values were then normalized to the wild-type split RNAP fused to ZA and ZB (data shown in FIG. 1d), which was assigned an arbitrary value of 100, allowing the values from each luminescence plot to be compared to one another. For the light-activated system, the experiment was performed identically, except upon outgrowth cells in the light condition were illuminated with a homemade blue LED lightbox and cultured at 25° C. and cells in the dark condition were cultured at 37° C.; this was done to maintain similar luciferase levels for non-light inducible controls used in both conditions. For the rapamycin inducible system, the experiment was performed identically, except upon outgrowth, rapamycin was added for 3 h, and then luminescence analyzed. Sample size (n=4 biological replicates for each condition) was determined by previous work using a similar in vivo luciferase reporter system, and provided excellent reproducibility both between biological replicates on a given day and between days of experimental replicates.

Phage-assisted continuous evolution (PACE). PACE was carried out to evolve the split T7 RNAP variants using a modified version of previously described methods (Pu, et al., 2015, the contents of which are incorporated by reference; and U.S. patent application Ser. No. 13/996,208, "Continuous directed evolution", published as US 2013/0345064A1, the contents of which are incorporated by reference). *E. coli*. strain S1030 were transformed by electroporation with combinations of the Positive Accessory Plasmid (posAP), Negative Accessory Plasmid (negAP), and mutagenesis plasmid (MP) (Dickinson, et al., 2014) (FIG. 6). 5 mL starter cultures were grown overnight in LB supplemented with antibiotics and 10 mM glucose. Chemostats (100 mL sterile bottles) containing 80 mL of Davis rich media (Carlson, et al., 2014) were inoculated with 2 mL of starter culture and grown at 37° C. with magnetic stir-bar agitation. At approximately OD600 1.0, fresh Davis rich media was pumped in at 60-80 mL h−1, with a waste needle set at 80 mL. 10 µL of phage were used to seed a fresh lagoon (20 mL flask with a rubber septum). To initiate the evolution, a monoclonal phage population was utilized. Waste needles were set to maintain the lagoon volume at 15-20 mL, and host cell cultures were flowed in at 15-17 mL h−1. Arabinose (10% w/v in water) was added directly to lagoons via syringe pump at 1.0 mL h−1 to induce mutagenesis. A lagoon sample was taken from the waste withdrawal line every 24 h, centrifuged, and stored at 4° C. A schematic of the complete evolutionary protocol is shown in FIG. 6. After the completion of each leg of the evolution, activity-dependent plaque assays were used to select the next evolutionary target, and the PACE experiment was again initiated as described, using 10 µL of phage from the previous endpoint of the evolution. The strength of the positive and negative selection pressures were varied by altering the ribosome binding sites (RBSs) (Ringquist, et al., 1992) controlling the expression of each of the C-terminal target fusions, gIII, and gIIIneg. Mixed selection pressures, indicated by listing multiple posAP/negAP sets for a given timepoint, were utilized as appropriate to enhance the likelihood of successful evolution (Pu, et al., 2015; Dickinson, et al., 2013; Leconte, et al., 2013).

Sequence and activity analysis of variants from PACE. Phage samples were boiled for 10 min to lyse the phage and release the genomes. PCR was then used to amplify the DNA library containing the N-terminal RNAP variants, which was then subcloned into vector p3-7 (FIG. 5). Single colonies were picked from the transformation and subjected to analysis by Sanger sequencing. The results of the sequence analysis during the course of the evolution are shown in FIG. 7. Variants N-29-1 and N-29-8 cloned into vector p3-7 were subjected to analysis by the luciferases assays as shown in FIG. 2d. In order to sequence any potential mutations that occurred in the peptide fusion in the phage, single plaques from an activity-independent plaque assay were picked, grown overnight, boiled, and then analyzed by Sanger sequencing.

Cell culture. HEK293T cells (ATCC) were maintained in DMEM [with 10% fetal bovine serum (FBS, Gibco/Life Technologies, Qualified US origin), 1% penicillin/streptomycin (P/S, Gibco/Life Technologies), high glucose, L-glutamine, phenol red, sodium pyruvate] obtained from Gibco or Hyclone. HEK293T cells are listed in the database of commonly misidentified cell lines maintained by ICLAC (available on the world wide web at iclac.org/databases/cross-contaminations/). We obtained fresh cells from ATCC, which were frozen down at an early passage (passage 5) in individual aliquots. The cells were then used for less than 25 passages for all experiments. Multiple biological replicates were performed with cells from different passages and freshly thawed aliquots. There was no testing for mycoplasma infection or further authentication because early passage cells were used for all experiments.

Imaging mammalian AR activation by fluorescence microscopy. HEK293T cells cultured in DMEM (with high glucose, glutamine, phenol red, pyruvate; Gibco/Life Technologies) supplemented with 10% fetal bovine serum (FBS, Gibco/Life Technologies, Qualified US origin) were plated on an 8-well coverglass slide (Labtek) and transfected with 600 ng of a rapa-T7 vector (pJin141 or p6-8) using 1.5 µL of Lipofectamine 2000 (ThermoFisher Scientific) using the standard protocol. For the rapa-T7-F30-2×dBroccoli (pJin141) experiments, 100 nM raprmycin or DMSO control was added along with 20 µM DHFB1-1T for 30 min prior to imaging. For the rapa-T7-mRNA(GFP) (p6-8) experiments, 10 nM rapamycin or DMSO control was added to the sample 20 h after transfection, and then incubated for an additional 24 h. The cells were imaged on an Olympus BX53 microscope using a GFP filter set and a 10× objective. Each image for a given condition was processed using identical conditions to adjust brightness and contrast to a level where background fluorescence was observed for control samples in ImageJ (Wayne Rasband, NIH).

Flow cytometry. HEK293T cells were cultured in DMEM (with high glucose, glutamine, phenol red, pyruvate; Gibco/Life Technologies) supplemented with 10% fetal bovine serum (FBS, Gibco/Life Technologies). The day prior to transfection, cells were passaged and plated at 50,000 cells per well in a 48 well plate (NEST Biotechnology). After 19 hours, 50 ng of the RFP plasmid (p3-62), 200 ng of the GFP plasmid (p1-53), and 400 ng of the rapa-T7-shRNA(GFP) vector (pJin140) were transfected into cells using 1.5 µL of Lipofectamine 2000 (ThermoFisher Scientific) using the standard protocol. 30 min after transfection, DMEM supplemented with FBS and either DMSO or rapamycin was added to the wells so the final rapamycin concentrations were 0 nM, 0.001 nM, 0.01 nM, 0.1 nM, 1 nM, and 10 nM. 29 h after transfection, the media was replaced with fresh media including the correct concentration of rapamycin. 44 h after transfection, the cells were trypsinized and suspended in DMEM supplemented with FBS and rapamycin, and then analyzed on a LSR-Fortessa 4-15 (BD digital instrument, 488 nM laser, 530/30 nM filter for GFP, and 610/20 nM filter for RFP). Mean GFP fluorescence intensity was calculated for HEK293T cells expressing RFP using FloJo software. Reported values are average mean GFP fluorescence intensity values taken from three separate replicate samples. Sample size (n=3 biological replicates for each condition) was determined by initial trial experiments to find the spread in the data.

Example 1

Biophysical Feasibility of Proximity-Dependent Split RNAP

Two key biophysical criteria for the inventors' proposed AR strategy are that fused protein domains do not sterically interfere with the split RNAP and that interactions of fused domains can influence the RNAP assembly process. The inventors chose to deploy T7 RNAP split at position 179 because, 1) the N-terminal half is as small as possible, 2) structural data indicates this position is solvent exposed and removed from the DNA-binding face of the protein, and 3) mutations that influence DNA promoter specificity are C-terminal to this position (Shis & Bennett, 2013; Dickinson, et al., 2013; Ellefson, et al., 2014). First, the inventors validated that the two RNAP halves spontaneously assemble using an E. coli luciferase reporter system (FIG. 1b, c, d; FIG. 5). Next, the inventors utilized known leucine zipper peptides that form a tight interaction with one another (ZA and ZB) (Ghosh, et al., 2000; Magliery, et al., 2005) as known PPI partners. Fusion of ZA or ZB to the N-terminal or C-terminal RNAP, respectively, did not dramatically affect spontaneous RNAP assembly, indicating that the split RNAP can tolerate fusions. Even more encouragingly, fusion of both RNAP halves to the interaction partners resulted in an ~5-fold enhancement in transcription, indicating additional pendant interactions enhance split RNAP assembly (FIG. 1d). A triple mutant of ZB that weakens the interaction (ZBneg) confirms the enhancement in transcription is due to the fused PPI. Although these data confirm that it is biophysically feasible to modulate the RNAP assembly process, the dynamic range of the system is inadequate. Therefore, the inventors turned their attention to engineering the split RNAP to be more dependent on the fused interaction partners.

Example 2

Development of a Continuous Evolution System to Optimize Split RNAPs for PPI Detection In order to develop split RNAPs as a platform for biosensor design, the RNAP assembly process needs to be more dependent on fused interaction partners. This involves tuning the affinity of the interface between the two RNAP halves while maintaining all of the other aspects of RNAP enzymatic function, including DNA binding, nucleotide binding, and RNA synthesis. Such a protein engineering problem presents substantial challenges, which can in principle be overcome by molecular evolution. Therefore, the inventors chose to deploy PACE, a rapid evolution system (Esvelt, et al., 2011), which has been used to evolve RNAP promoter specificity, protein-DNA interactions, protease activities, and protein-protein interactions (Packer & Liu, 2015; Dickinson, et al., 2013; Esvelt, et al., 2011; Badran, et al., 2016; Carlson, et al., 2014; Dickinson, et al., 2014; Hubbard, et al., 2015; Leconte, et al., 2013). Briefly, PACE involves providing an evolving gene of interest to M13 bacteriophage, linking the life cycle of the phage to a desired activity of interest to be evolved in the target gene, and then propagating the virus until the activity evolves. Expression of gIII, a required phage gene, is the basis of the life cycle link.

The inventors envisioned a new PACE system for the evolution of selective assembly of split RNAPs using the leucine zipper peptides as a model PPI. In this system, phage would carry an evolving N-terminal RNAP variant fused to ZA, and the host E. coli cells would express two different C-terminal variants, each with orthogonal DNA promoter specificity, and each fused to either ZB or ZB-neg. Assembly of the evolving phage-carried N-terminal RNAP with the ZB-fused C-terminal RNAP would result in enhanced phage propagation, while assembly with the ZBneg-fused RNAP would decrease phage propagation. The inventors postulated that such a simultaneous dual positive/negative selection would result in the most robust evolutionary outcomes. Critically, the inventors would use relatively long (6-8 amino acids), unstructured linkers tethering the fusion proteins to the RNAP halves, enforcing the evolution of a mechanism of proximity-dependent RNAP assembly that is less dependent on geometry and linker composition, which the inventors hypothesized would result in a more versatile biosensor platform.

To develop the new PACE system, M13 phage were engineered by replacing gIII with N-terminal T7 RNAP fused to ZA, which is the target of the evolution. E. coli were engineered with a "Positive Accessory Plasmid" (posAP) that expresses a C-terminal T7 RNAP variant (C-term CGG RNAP) fused to ZB, which contains 5 point mutations that allow it to act selectively on the "CGG" promoter over the T7 promoter (Segall-Shapiro, et al., 2014; Ellefson, et al., 2014), and CGG promoter-driven gIII The E. coli cells were also engineered with a second "Negative Accessory Plasmid" (negAP), which expresses the wildtype C-terminal T7 RNAP fused to ZBneg and a dominant negative form of gIII under control of the T7 promoter (Carlson, et al., 2014). Therefore, if an evolving N-term RNAP variant assembles efficiently with both of the T7 and CGG C-term RNAP halves, phage production is blocked. However, phage encoding N-term variants that selectively assemble with the ZB fused CGG C-term half will replicate more efficiently, and continue to mutate until the interaction is optimized (FIG. 2a). The key is that the only difference between the positive and negative selection is whether or not the fused peptides interact based on 3 point mutations in ZBneg compared to ZB, and the 5 mutations that alter DNA binding of the CGG C-terminal RNAP, which are not at the protein-protein interface and are not expected to alter RNAP assembly.

Example 3

Evolution of a Proximity Dependent Split RNAP Using PACE

After cloning and validating the system components, the inventors initiated PACE. The positive and negative selection pressures were modified by carefully tuning the system components (FIG. 2b, FIG. 6) and the progress of the evolution was monitored by activity-dependent plaque assays and genetic analysis of the evolving phage (Supplementary FIG. 4). Specifically, the inventors altered the concentrations of the on-target and off-target interactions, and the strength of selection of the RNA output, by tuning the ribosome binding sites (RBSs) controlling each system component. After each 3-4 days of PACE on a given target, the inventors would use activity-dependent plaque assays to decide the subsequent evolutionary targets. This process continued for 29 days, after which time the N-terminal RNAP converged on two main genotypes, a 6-mutation (N-29-1) and a 7-mutation (N-29-8) variant (FIG. 2c), with several of the mutations near the interface between the two halves of the split RNAP (FIG. 2d). T7 RNAP undergoes dramatic conformational changes during the course of its enzymatic activity (Steitz, et al., 2009). Additionally, several mutations that are highly enriched exist in either solvent-exposed regions of the structure, or even less predictably, at the protein-DNA interface. This suggests epistatic interactions between mutations that tune the protein-protein interface with key mutations elsewhere in the protein, further illustrating why the inventors' unbiased directed evolution strategy is the optimal approach for tuning a complex molecular machine like an RNAP.

Assaying the two primary variants that emerged from PACE in the transcription reporter system revealed that the background level of transcription with the ZBneg control was dramatically decreased, almost to undetectable levels (FIG. 2e). However, the overall activity in the presence of the ZA-ZB interaction also decreased. Further genetic analysis revealed that the ZA leucine zipper protein, which the inventors assumed was already fully optimized for interaction with ZB, also evolved during PACE, converging on two leucine to isoleucine mutations. Inclusion of the two ZA mutations into N-29-1 and N-29-8 resulted in a dramatic enhancement in assembly of the split RNAP with the ZA-ZB partners, but maintained low levels of background with the ZBneg control (FIG. 2e). These results indicate that the assembly of the evolved RNAP is not only dependent on fused interaction partners, but is dynamically sensitive to the affinity of the interaction. Moreover, these data also demonstrate that this new split RNAP PACE system can be deployed to optimize biomolecular interactions, similar to recent 2-hybrid PACE systems (Badran, et al., 2016), but permitting robust negative selection. Most importantly, PACE yielded the N-terminal RNAP variant N-29-1 for the AR strategy, which has an ~40-fold dynamic range of RNA synthesis based on fused PPIs.

Example 4

Deploying Evolved AR System to Generate Light and Small Molecule Sensors

With the optimized and validated AR system for PPIs in hand, the inventors next sought to explore the generality of the approach. The inventors wanted to develop inducible PPI systems, and therefore targeted light and small molecule-activated AR sensors. To create a light-activated RNAP, the inventors appended the light-oxygen-voltage 2 (LOV2)-SsrA fusion variant and SspB from the recently developed improved light induced dimer (iLID-nano) system (Gultas, et al., 2015) to the C-terminal RNAP and N-29-1 (FIG. 3a) without any additional optimization of linkers, geometry, or concentrations, and assayed the fusions in E. coli. Illumination with blue LED light, which induces dimerization of the iLID-nano system, resulted in a 26-fold enhancement in transcriptional output of the light-activated AR, while control fusions do not show a light response (FIG. 3b). This dynamic range of a completely non-optimized system is impressive because the actual light induced difference in affinity of the iLID-nano system proteins is only 36-fold (Guntas, et al., 2015).

Next, to further explore the versatility of ARs to detect a 3-hybrid-like interaction, the inventors sought to engineer a small molecule-activated RNAP. The rapamycin-induced dimerization of FRB and FKBP has served as a workhorse small molecule-induced dimerization system for a multitude of applications (Rivera, et al., 1996), and served as the next target for the inventors' split RNAP system. While there are existing methods to control RNA synthesis with small molecules in prokaryotic systems, there are far fewer that function well in mammalian systems (Gossen & Bujard, 1992; Paulmurugan, et al., 2009), and many have issues with signal-to-noise rations and background activity. Therefore, the inventors envisioned that a small molecule-inducible RNAP would not only allow us to assay the capabilities of the inventors' new approach, but would provide the community with a new tool to control gene expression in diverse systems. The inventors replaced the peptide fusions on the E. coli. expression vectors for the C-terminal RNAP and N-29-1 with the FKBP and FRB, again without any optimization of linkers, concentration, geometry, or any other system component (FIG. 3c). As seen in FIG. 3d, a dramatic, dose-responsive increase in RNA synthesis is observed in the in vivo luciferase transcription reporter assay upon treatment with rapamycin, with a 340-fold enhancement in RNA synthesis and essentially undetectable background. The robust improvement in dynamic range of the small molecule AR system is potentially due to steric interference lowering the background in the absence of rapamycin or a lower affinity of the FRB and FKBP in the absence of rapamycin compared to the ZA/ZB leucine zipper partners. Collectively, these data demonstrate the ability to simply swap in new binding domains to the AR system with minimal optimization to create biosensors.

Example 5

ARs can Generate Fluorescent RNA, Protein, and RNAi in Mammalian Cells

Finally, the inventors assayed the ability of the ARs to function in mammalian cells, using the rapamycin-inducible system as an exemplar. The inventors generated the "rapa-T7" vector, which expresses both the rapamycin-inducible AR along with a T7 promoter-driven gene of interest (goi) output (FIG. 4a). To validate that RNA was being generated, the inventors first deployed a fluorescent aptamer (F30-2× dBroccoli) (Filonov, et al., 2015) as the goi output of the rapa-T7 vector, allowing the visualization of RNA synthesis using fluorescence microscopy. In the absence of rapamycin, there is no detectible fluorescence from HEK293T cells transformed with rapa-T7-F30-2×dBroccoli. However, treatment with 100 nM rapamycin for 30 min results in a robust enhancement in intracellular fluorescence (FIG. 4b, Supplementary FIG. 5), demonstrating the fast kinetics of a T7 RNAP-based biosensor. Next, to assay whether the inventors could trigger protein production as the AR output, the inventors set mRNA for green fluorescent protein (GFP) as the goi on the rapa-T7 vector, allowing us to monitor protein synthesis by fluorescence microscopy. Again, the background fluorescence level of rapa-T7-mRNA(GFP) transfected cells was low in the absence of rapamycin, but addition of 10 nM rapamycin resulted in a dramatic enhancement in GFP fluorescence (FIG. 4c, Supplementary FIG. 6). Finally, to test whether ARs could trigger genetic changes and interact with the cell in a biologically relevant manner, the inventors tested whether RNAi is a viable output. For this, the inventors set shRNA targeting GFP in the rapa-T7 vector, cotransfected cells with both a GFP expression vector and the rapa-T7-shRNA(GFP) vector, and analyzed GFP production by flow cytometry. Induction with rapamycin resulted in a dose-dependent knockdown of GFP signal (FIG. 4d). Collectively, these results demonstrate that ARs function in mammalian cells and can trigger a variety of different outputs via the RNA signal.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Badran, A. H. et al. Continuous evolution of *Bacillus thuringiensis* toxins overcomes insect resistance. Nature, (2016).

Baker, K. et al. Chemical complementation: a reaction-independent genetic assay for enzyme catalysis. Proc Natl Acad Sci USA 99, 16537-16542, (2002).

Benenson, Y. RNA-based computation in live cells. Curr Opin Biotechnol 20, 471-478, (2009).

Brophy, J. A. & Voigt, C. A. Principles of genetic circuit design. Nat Methods 11, 508-520, (2014).

Carlson, J. C., Badran, A. H., Guggiana-Nilo, D. A. & Liu, D. R. Negative selection and stringency modulation in phage-assisted continuous evolution. Nat Chem Biol 10, 216-222, (2014).

Church, G. M., Elowitz, M. B., Smolke, C. D., Voigt, C. A. & Weiss, R. Realizing the potential of synthetic biology. Nat Rev Mol Cell Biol 15, 289-294, (2014).

Copeland, M. F., Politz, M. C., Johnson, C. B., Markley, A. L. & Pfleger, B. F. A transcription activator-like effector (TALE) induction system mediated by proteolysis. Nat Chem Biol, (2016).

Culler, S. J., Hoff, K. G. & Smolke, C. D. Reprogramming cellular behavior with RNA controllers responsive to endogenous proteins. Science 330, 1251-1255, (2010).

Dickinson, B. C., Leconte, A. M., Allen, B., Esvelt, K. M. & Liu, D. R. Experimental interrogation of the path dependence and stochasticity of protein evolution using phage-assisted continuous evolution. Proc Natl Acad Sci USA 110, 9007-9012, (2013).

Dickinson, B. C., Packer, M. S., Badran, A. H. & Liu, D. R. A system for the continuous directed evolution of proteases rapidly reveals drug-resistance mutations. Nat Commun 5, 5352, (2014).

Ellefson, J. W. et al. Directed evolution of genetic parts and circuits by compartmentalized partnered replication. Nat Biotechnol 32, 97-101, (2014).

Esvelt, K. M., Carlson, J. C. & Liu, D. R. A system for the continuous directed evolution of biomolecules. Nature 472, 499-503, (2011).

Feng, J. et al. A general strategy to construct small molecule biosensors in eukaryotes. Elife 4, (2015).

Fields, S. & Song, O. A novel genetic system to detect protein-protein interactions. Nature 340, 245-246, (1989).

Filonov, G. S., Kam, C. W., Song, W. & Jaffrey, S. R. In-gel imaging of RNA processing using broccoli reveals optimal aptamer expression strategies. Chem Biol 22, 649-660, (2015).

Ghosh, I., Hamilton, A. D. & Regan, L. Antiparallel Leucine Zipper-Directed Protein Reassembly: Application to the Green Fluorescent Protein. J Am Chem Soc 122, 5658-5659, (2000).

Gibson, D. G. et al. Enzymatic assembly of DNA molecules up to several hundred kilobases. Nat Methods 6, 343-345, (2009).

Gossen, M. & Bujard, H. Tight control of gene expression in mammalian cells by tetracycline-responsive promoters. Proc Natl Acad Sci USA 89, 5547-5551, (1992).

Green, A. A., Silver, P. A., Collins, J. J. & Yin, P. Toehold switches: de-novo-designed regulators of gene expression. Cell 159, 925-939, (2014).

Guntas, G. et al. Engineering an improved light-induced dimer (iLID) for controlling the localization and activity of signaling proteins. Proc Natl Acad Sci USA 112, 112-117, (2015).

Hu, C. D. & Kerppola, T. K. Simultaneous visualization of multiple protein interactions in living cells using multicolor fluorescence complementation analysis. Nat Biotechnol 21, 539-545, (2003).

Hubbard, B. P. et al. Continuous directed evolution of DNA-binding proteins to improve TALEN specificity. Nat Methods 12, 939-942, (2015).

Kerppola, T. K. Visualization of molecular interactions using bimolecular fluorescence complementation analysis: characteristics of protein fragment complementation. Chem Soc Rev 38, 2876-2886, (2009).

Konermann, S. et al. Optical control of mammalian endogenous transcription and epigenetic states. Nature 500, 472-476, (2013).

Leconte, A. M. et al. A population-based experimental model for protein evolution: effects of mutation rate and selection stringency on evolutionary outcomes. Biochemistry 52, 1490-1499, (2013).

Lee, J. H. et al. Highly multiplexed subcellular RNA sequencing in situ. Science 343, 1360-1363, (2014).

Lienert, F., Lohmueller, J. J., Garg, A. & Silver, P. A. Synthetic biology in mammalian cells: next generation research tools and therapeutics. Nat Rev Mol Cell Biol 15, 95-107, (2014).

Magliery, T. J. et al. Detecting protein-protein interactions with a green fluorescent protein fragment reassembly trap: scope and mechanism. J Am Chem Soc 127, 146-157, (2005).

Martin, F. Fifteen years of the yeast three-hybrid system: RNA-protein interactions under investigation. Methods 58, 367-375, (2012).

Nunez, J. K., Harrington, L. B. & Doudna, J. A. Chemical and Biophysical Modulation of Cas9 for Tunable Genome Engineering. ACS Chem Biol, (2016).

Packer, M. S. & Liu, D. R. Methods for the directed evolution of proteins. Nat Rev Genet 16, 379-394, (2015).

Paulmurugan, R. et al. A novel estrogen receptor intramolecular folding-based titratable transgene expression system. Mol Ther 17, 1703-1711, (2009).

Polstein, L. R. & Gersbach, C. A. A light-inducible CRISPR-Cas9 system for control of endogenous gene activation. Nat Chem Biol 11, 198-200, (2015).

Pu, J., Chronis, I., Ahn, D. & Dickinson, B. C. A Panel of Protease-Responsive RNA Polymerases Respond to Biochemical Signals by Production of Defined RNA Outputs in Live Cells. J Am Chem Soc 137, 15996-15999, (2015).

Putz, U., Skehel, P. & Kuhl, D. A tri-hybrid system for the analysis and detection of RNA-protein interactions. Nucleic Acids Res 24, 4838-4840, (1996).

Ringquist, S. et al. Translation initiation in *Escherichia coli*: sequences within the ribosome-binding site. Mol Microbiol 6, 1219-1229, (1992).

Rivera, V. M. et al. A humanized system for pharmacologic control of gene expression. Nat Med 2, 1028-1032, (1996).

Ruder, W. C., Lu, T. & Collins, J. J. Synthetic biology moving into the clinic. Science 333, 1248-1252, (2011).

Segall-Shapiro, T. H., Meyer, A. J., Ellington, A. D., Sontag, E. D. & Voigt, C. A. A 'resource allocator' for transcription based on a highly fragmented T7 RNA polymerase. Mol Syst Biol 10, 742, (2014).

SenGupta, D. J. et al. A three-hybrid system to detect RNA-protein interactions in vivo. Proc Natl Acad Sci U S A 93, 8496-8501, (1996).

Shekhawat, S. S. & Ghosh, I. Split-protein systems: beyond binary protein-protein interactions. Curr Opin Chem Biol 15, 789-797, (2011).

Shis, D. L. & Bennett, M. R. Library of synthetic transcriptional AND gates built with split T7 RNA polymerase mutants. Proc Natl Acad Sci USA 110, 5028-5033, (2013).

Steitz, T. A. The structural changes of T7 RNA polymerase from transcription initiation to elongation. Curr Opin Struct Biol 19, 683-690, (2009).

Winkler, W. C. & Breaker, R. R. Regulation of bacterial gene expression by riboswitches. Annu Rev Microbiol 59, 487-517, (2005).

Yen, L. et al. Exogenous control of mammalian gene expression through modulation of RNA self-cleavage. Nature 431, 471-476, (2004).

Zamft, B. M. et al. Measuring cation dependent DNA polymerase fidelity landscapes by deep sequencing. PLoS One 7, e43876, (2012).

Zhang, J., Jensen, M. K. & Keasling, J. D. Development of biosensors and their application in metabolic engineering. Current Opinion in Chemical Biology 28, 1-8, (2015).

U.S. patent application Ser. No. 13/996,208, Continuous directed evolution.

The invention claimed is:

1. A system comprising:
a) a first polymerase domain attached to a first interaction component;
b) a second polymerase domain attached to a second interaction component;
c) a nucleic acid construct comprising a reporter gene under the control of a first heterologous promoter responsive to polymerase activity from the first and second polymerase domains when the first and second interaction components interact,
wherein the first polymerase domain comprises amino acids 1-179 of a T7 RNA polymerase and the second polymerase domain comprises amino acids 180-883 of a T7 RNA polymerase; wherein the system further comprises a negative control nucleic acid encoding a polypeptide that does not interact with the first or second interaction component; and wherein the polypeptide encoded by the negative control nucleic acid is attached to an alternate first polymerase domain comprising amino acids 1-179 of a T7 RNA polymerase or an alternate second polymerase domain comprising amino acids 180-883 of a T7 RNA polymerase and the system further comprises a second heterologous promoter responsive to polymerase activity from the interaction of the first and alternate second polymerase domains or the alternate first and the second polymerase domains.

2. The system of claim 1, wherein the first and second interaction components are peptides or polypeptides.

3. The system of claim 1, wherein the reporter gene is encoded by at least one reporter plasmid.

4. The system of claim 1, wherein the first polymerase domain and the second polymerase domain are encoded by separate expression plasmids.

5. The system of claim 1, wherein a second reporter gene is under the control of the second heterologous promoter.

6. The system of claim 1, wherein the first and second interaction components dimerize or are brought into proximity by interaction with a third interaction component.

7. The system of claim 6, wherein the third interaction component is a small molecule.

8. The system of claim 1, wherein the first and second polymerase domains are separate polypeptide chains and wherein each of the first and second polymerase domains are linked to one of the first and second interaction components as fusion proteins.

9. The system of claim 1, wherein the system comprises at least one expression plasmid comprising a phage gene.

10. The system of claim 1, wherein the first heterologous promoter is a T7 promoter.

11. The system of claim 1, wherein the reporter gene encodes a RNA nanostructure, a mRNA encoding a reporter protein or a RNAi molecule.

12. A cell comprising the system of claim 1.

13. A system comprising:
   a) a first polymerase domain attached to a first interaction component;
   b) a second polymerase domain attached to a second interaction component;
   c) a nucleic acid construct comprising a reporter gene under the control of a first heterologous promoter responsive to polymerase activity from the first and second polymerase domains when the first and second interaction components interact, wherein the first polymerase domain comprises amino acids 1-179 of SEQ ID NOs:4, 6, or 8, and the second polymerase domain comprises the amino acid sequence of SEQ ID NO:2; and wherein the system further comprises a negative control nucleic acid encoding a polypeptide that does not interact with the first or second interaction component; and wherein the polypeptide encoded by the negative control nucleic acid is attached to an alternate first polymerase domain comprising amino acids 1-179 of a T7 RNA polymerase or an alternate second polymerase domain comprise, comprising amino acids of a T7 RNA polymerase and the system further comprises a second heterologous promoter responsive to polymerase activity from the interaction of the first and alternate second polymerase domains or the alternate first and the second polymerase domains.

* * * * *

UNITED STATES PATENT AND TRADEMARK OFFICE
CERTIFICATE OF CORRECTION

PATENT NO. : 11,913,081 B2
APPLICATION NO. : 16/305298
DATED : February 27, 2024
INVENTOR(S) : Bryan C. Dickinson et al.

It is certified that error appears in the above-identified patent and that said Letters Patent is hereby corrected as shown below:

In the Specification

In Column 1, Line 29, please delete "This invention was made with government support under grant number CA014599 awarded by the National Institutes of Health. The government has certain rights in the invention." and insert --This invention was made with government support under CA014599 awarded by the National Institutes of Health. The government has certain rights in the invention.-- therefor.

Signed and Sealed this
Seventh Day of May, 2024

Katherine Kelly Vidal
Director of the United States Patent and Trademark Office